United States Patent [19]
Kling et al.

[11] Patent Number: 5,807,984
[45] Date of Patent: Sep. 15, 1998

[54] OLIGOPEPTIDES, THE PREPARATION AND USE THEREOF

[75] Inventors: Andreas Kling, Mannheim; Bernd Janssen, Ludwigshafen; Wilhelm Amberg, Friedrichsdorf, all of Germany; Andreas Haupt, Westborough; Kurt Ritter, Newton, both of Mass.; Ernst Buschmann, Ludwigshafen, Germany; Harald Bernard, Bad Dürkheim, Germany; Stefan Müller, Speyer, Germany; Thomas Zierke, Böhl-Iggelheim, Germany; Teresa Barlozzari, Wellsley, Mass.; Monika de Arruda, Shrewsbury, Mass.; Simon Robinson, Sterling, Mass.

[73] Assignee: BASF Aktienegesellschaft, Germany

[21] Appl. No.: 554,897

[22] Filed: Nov. 9, 1995

[51] Int. Cl.$^6$ .............................. C07K 7/06; A61K 38/03
[52] U.S. Cl. .............................. 530/330; 530/329; 514/17
[58] Field of Search .............................. 514/17; 530/330, 530/329

[56] References Cited

U.S. PATENT DOCUMENTS

| | | | |
|---|---|---|---|
| 4,816,444 | 3/1989 | Petit et al. | 514/17 |
| 4,879,278 | 11/1989 | Petttit et al. | 514/17 |
| 5,502,032 | 3/1996 | Haupt et al. | 514/17 |
| 5,504,191 | 4/1996 | Pettit et al. | 530/330 |
| 5,530,097 | 6/1996 | Pettit et al. | 530/330 |

FOREIGN PATENT DOCUMENTS

| | | |
|---|---|---|
| 0 398 558 | 11/1990 | European Pat. Off. . |
| 0 598 129 | 5/1994 | European Pat. Off. . |

OTHER PUBLICATIONS

Rudinger, J 'Characteristics of amino acids as components of peptide hormones sequence' in Peptide Hormones, (ed. J.A. Parsons). University Park Press, Baltimore, pp. 1–7, 1976.

Smith et al. 'Pre–clinical anti–tumor activity of novel water soluble Dolastatin 15 analog (LU103793)', Proceedings of the American Association for Cancer Research Annual Meeting 36(0). 1995. p. 393 #2345.

Pettit, G. R., et al., "The Isolation and Structure of a Remarkable Marine Animal Antineoplastic Constituent: Dolastatin 10," J, Am. Chem. Soc., 109: 6883–6885 (1987).

Bai, R., et al., "Structure–Activity Studies with Chiral Isomers and with Segments of the Antimitotic Marine Peptide Dolastatin 10," Biochemical Pharmacology, 40(8): 1859–1864 (1990).

Pettit, G. R, et al., "Antineoplastic Agents. 220. Synthesis of Natural (–)–Dolastatin 15, " J. Am. Chem. Soc., 113: 6692–6693 (1991).

Pettit, G. R., et al., "Isolation and Structure of the Cytostatic Linear Depsipeptide Dolastatin 15," J. Org. Chem., 54: 6005–6006 (1989).

Bai, R., et al., "Dolastatin 15, a potent antimitotic depsipeptide derived from *Dolabella auricularia*. Interaction with tubulin and effects on cellular microtubules," 1–Pharamacology Abstract 117: 103735g p. 41 (1992).

Pettit, G. R., et al., "Isolation and Structure of the Cytostatic Depsipeptide Dolastatin 13 from the Sea Hare *Dolabella auricularia*," J. Am. Chem. Soc., 111(3): 5015–5017 (1989).

Pettit, G. R., et al., "Antineoplastic agents 337. Synthesis of Dolastatin–10 Structural Modifications," Anti–Cancer Drug Design, 10: 529–544 (1995).

Miyazaki, K., et al., "Synthesis and Anti–Tumor Activity of Novel Dolastatin–10 Analogs," Chem. Pharm. Bull., 43(10: 1706–1718 (1995).

*Primary Examiner*—Cecilia J. Tsang
*Assistant Examiner*—Anish Gupta
*Attorney, Agent, or Firm*—Hamilton, Brook, Smith & Reynolds, P.C.

[57] ABSTRACT

Novel peptides of the formula

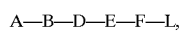

A—B—D—E—F—L, wherein A, B, D, E, F, and L have the meanings stated in the specification, and their preparation are disclosed. The novel compounds are suitable for controlling diseases.

5 Claims, No Drawings

OLIGOPEPTIDES, THE PREPARATION AND USE THEREOF

It is known that peptides isolated from marine origin like Dolastatin-10 (U.S. Pat. No. 4,816,444) and Dolastatin-15 (EP-A-398558) show potent cell growth inhibitory activity [cf.: Biochem. Pharmacology 40, 1859–64 (1990); J. Natl. Cancer Inst. 85, 483–88 (1993) and references cited therein]. Based upon interesting results in experimental tumor systems in vivo further preclinical evaluation of these natural products is currently under way to initiate clinical studies in cancer patients. Due to laborious purification processes from scarce natural sources alternative access to these peptides has been investigated by synthetic routes [cf.: Tetrahedron 50, 5345–60 (1994) Tetrahedron 49, 1913–24 (1993); Tetrahedron 48, 4115–22 (1992) and references cited therein].

Since the natural products show disadvantages as poor solubility in aqueous solvents and costly building blocks, structural modifications have been investigated [cf.: Bioorganic & Med. Chem. Lett. 4, 1947–50 (1994); WO 93 03054; JP-A-06234790, EP (O.Z. 43202)].

The invention described herein provides novel oligopeptides and derivatives thereof which offer a surprisingly improved therapeutic potential for the treatment of neoplastic diseases as compared to Dolastatin-10 and -15 with activity even in MDR resistant tumor systems and with an unpredicted high solubility in aqueous solvents. Furthermore, the compounds of the present invention may be conveniently synthesized as described below in detail.

Compounds of the present invention include peptides of the formula I

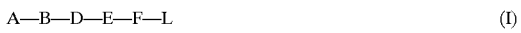

$$A{-}B{-}D{-}E{-}F{-}L \qquad (I)$$

and the salts thereof with physiologically tolerated acids, wherein A, B, D, E, F and L have the following meanings:

A:

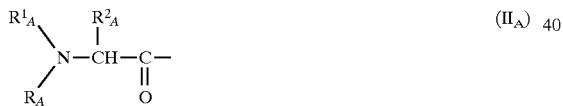

$(II_A)$ where $R_A$ is hydrogen, $C_{1-3}$-alkyl which can be substituted by 1 to 3 fluorine atoms or cyclopropyl which can be substituted by 1 to 3 fluorine atoms, $R^1_A$ is $C_{1-3}$-alkyl which can be substituted by 1 to 3 fluorine atoms or cyclopropyl which can be substituted by 1 to 3 fluorine atoms, $R^2_A$ is $C_{1-5}$-alkyl which can be substituted by 1 to 3 fluorine atoms, or $C_{3-5}$-cycloalkyl which can be substituted by 1 to 3 fluorine atoms, or

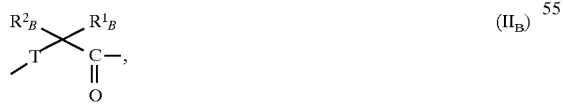

$(II_B)$ where either T is an NH group,
$R^1_B$ is hydrogen,
$R^2_B$ is $C_{1-6}$-alkyl, $C_{3-6}$-cycloalkyl, methoxymethyl, 1-methoxyethyl or 1-methylvinyl, or
$R^1_B$ and $R^2_B$ together are an isopropylidene group, or T is an oxygen atom,
$R^1_B$ is hydrogen and
$R^2_B$ is $C_{1-6}$-alkyl;

D:

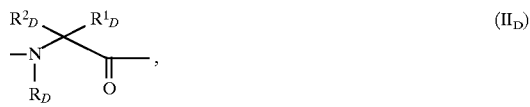

$(II_D)$ where $R_D$ is hydrogen, $C_{1-3}$-alkyl which can be substituted by 1 to 3 fluorine atoms or cyclopropyl which can be substituted by 1 to 3 fluorine atoms, $R^1_D$ is hydrogen and $R^2_D$ is $C_{1-5}$-alkyl, cyclo-propyl, methoxymethyl, 1-methoxyethyl or 1-methyl-vinyl, or

E:

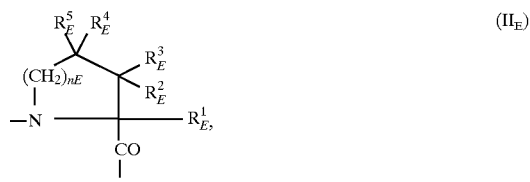

$(II_E)$ where $n_E$ is 0, 1 or 2, $R^1_E$ is hydrogen or $C_{1-3}$-alkyl which can be substituted by 1 to 3 fluorine atoms or cyclopropyl which can be substituted by 1 to 3 fluorine atoms, $R^2_E$ and $R^3_E$ are, independently of one another, hydrogen or a methyl group, $R^4_E$ is hydrogen, a hydroxy, methoxy or ethoxy group or a fluorine atom, and $R^5_E$ is hydrogen or a fluorine atom or, if $n_E$ is 1, $R^3_E$ and $R^4_E$ together are a bond, or $R^4_E$ and $R^5_E$ are a doubly bonded oxygen radical, or, if $n_E$ is 2, $R^1_E$ and $R^2_E$ together are a bond;

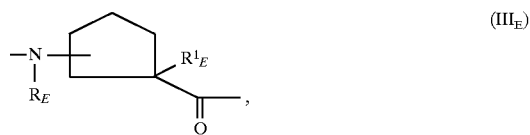

$(III_E)$ where $R_E$ is hydrogen or a methyl or ethyl group, and $R^1_E$ is hydrogen, $C_{1-3}$-alkyl which can be substituted by 1 to 3 fluorine atoms or cyclopropyl which can be substituted by 1 to 3 fluorine atoms, or E a residue of the formula

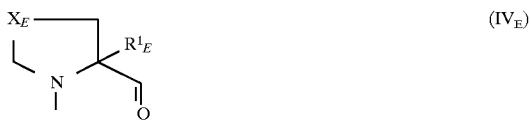

$(IV_E)$ wherein $X_E$ is an oxygen or a sulfur atom

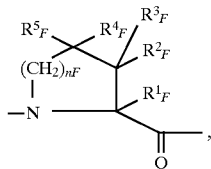

(II$_F$)

where
$n_F$ is 0, 1 or 2,
$R^1_F$ is hydrogen or $C_{1-3}$-alkyl which can be substituted by 1 to 3 fluorine atoms or cyclopropyl which can be substituted by 1 to 3 fluorine atoms,
$R^2_F$ and $R^3_F$ are, independently of one another, hydrogen or a methyl group,
$R^4_F$ is hydrogen, a hydroxy, methoxy or ethoxy group or a fluorine atom, and
$R^5_F$ is hydrogen or a fluorine atom or, if $n_F$ is 1, $R^3_F$ and $R^4_F$ together are a bond, or

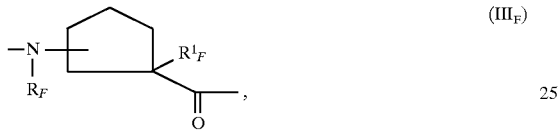

(III$_F$)

where
$R_f$ is hydrogen or a methyl or ethyl group, and
$R^1_F$ is $C_{1-3}$-alkyl which can be substituted by 1 to 3 fluorine atoms or cyclopropyl which can be substituted by 1 to 3 fluorine atoms, or

F:

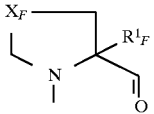

wherein $X_F$ is oxygen or sulfur
F: an N-methylglycyl, N-ethylglycyl or -alanyl radical,
L: a substituted or unsubstituted, hydroxylamino, or oxime residue.

In one embodiment, L is a radical of the formula I$_L$

—OR$_L$(I$_L$) 

wherein $R_L$ is a $C_{3-10}$-cycloalkyl, $C_{2-18}$-methylalkenyl, $C_{5-16}$-alkyl or $C_{1-15}$-alkylcarboxy-$C_{1-10}$-alkyl group, which can, optionally, be substituted by from 1 to 5 halogen atoms. $R_L$ can also be the radical —(CH$_2$)$_{aL}$—R$^1_L$ where a$_L$ is 1, 2 or 3. $R^1_L$ is a saturated or partially unsaturated $C_{3-10}$-carbocycle or a saturated or partially unsaturated $C_{3-10}$ cyclic radical which, in addition to carbon atoms, includes one or more heteroatoms selected from among oxygen, nitrogen and sulfur as ring members. In saturated systems which Include a nitrogen atom, the nitrogen atom can be bonded to a $C_{1-4}$-alkyl, $C_{1-4}$-acyl, $C_{1-4}$-alkoxyacyl, benzyl or benzoyl group.

$R_L$ can also be the radical —[CH$_2$—CH═C(CH$_3$)—CH$_2$]$_{bL}$—H where b$_L$ is 1–4. $R_L$ can also be the radical —(CH$_2$—CH$_2$—O)$_{dL}$—CH$_3$, wherein d$_L$ is 1–5.

If $R_L$ is —(CH$_2$)$_{eL}$-aryl, eL is 0, 1, 2 or 3 and then aryl is preferably phenyl or naphthyl, and suitable substituents are: halogen atoms, preferably fluorine, bromine or chlorine, $C_1$–$C_4$-alkyl groups, trifluoromethyl, $C_1$–$C_4$-alkoxy groups, trifluoromethoxy, dioxymethylene or -ethylene, a nitro or cyano group, $C_1$–$C_4$-alkoxycarbonyl, a $C_1$–$C_7$-alkylsulfonyl group, an amino or $C_1$–$C_7$-dialkylamino group in which the alkyl radicals can also together form a heterocycle. Hetaryl is preferably a 5- to 6-membered ring system which preferably contains nitrogen, oxygen and/or sulfur atoms and may be fused to a benzene ring, such as the imidazole, pyrrole, thiophene, furan, thiazole, oxazole, pyrazole, 1,2,4- or 1,2,3-triazole, oxadiazole, thiadiazole, isoxazole, isothiazole, pyrazine, pyridazine, pyrimidine, pyridine, benzofuran, benzothiophene, benzimidazole, benzothiazole, benzopyran, indole, isoindole, indazole or quinoline residue, the preferred substituents being $C_1$–$C_4$-alkyl groups, or the hydroxyl or phenyl radical.

If $R_L^2$ is substituted aryl or methylaryl, the substituents preferably have the following meanings:
halogen atoms, $C_1$–$C_4$-alkyl, trifluoromethyl, $C_1$–$C_4$-alkoxy groups, trifluoromethoxy, dioxymethylene or -ethylene, a nitro or cyano group, $C_1$–$C_4$-alkoxycarbonyl, a $C_1$–$C_7$-alkylsulfonyl group, an amino or $C_1$–$C_7$-dialkylamino group, in which the alkyl radicals can also together form a heterocycle.

If $R_L^3$ is substituted aryl or methylaryl, the substituents preferably have the following meanings:
halogen atoms, $C_1$–$C_4$-alkyl, trifluoromethyl, $C_1$–$C_4$-alkoxy groups, trifluoromethoxy, dioxymethylene or -ethylene, a nitro or cyano group, $C_1$–$C_4$-alkoxycarbonyl, a $C_1$–$C_7$-alkylsulfonyl group, an amino or $C_1$–$C_7$-dialkylamino group, in which the alkyl radicals can also together form a heterocycle.

Another group of compounds according to the invention includes peptide derivatives of the formula I where
L is a hydroxylamine residue of the formula

(V$_L$)

where
$R_L^5$ is hydrogen, straight-chain or branched $C_1$–$C_8$-alkyl which can be substituted by up to 6 halogen atoms, preferably fluorine, or $C_{3-10}$-cycloalkyl or $C_{1-4}$-alkyl-$C_{3-10}$-cycloalkyl, substituted or unsubstituted aryl or hetaryl or substituted or unsubstituted $C_{1-4}$-alkylaryl with the substituents having the meanings stated for $R_L$, and
$R_L^6$ has one of the meanings stated for $R_L^5$, where $R_L^5$ and $R_L^6$ are not both hydrogen, or
$R_L^5$ and $R_L^6$ together with the N atom form a 5-, 6- or 7-membered heterocycle, and the salts thereof with physiologically tolerated acids.

Another group of compounds according to the invention includes peptide derivatives of the formula I as claimed in claim 1, where L is an oxime residue of the formula VI_L $$-O-N=C\begin{matrix}R_L^6\\R_L^5\end{matrix} \quad (VI_L)$$

where
$R_L^5$ and $R_L^6$ have the abovementioned meanings, or $$=C\begin{matrix}R_L^6\\R_L^5\end{matrix}$$

$R_L^5$ and $R_L^6$ together with the C atom form a 3- to 7-membered cyclic system which may be aromatic-fused, and the salts thereof with physiologically tolerated acids.

Preferred cyclic systems are:

[cyclic systems shown: cyclohexylidene, thiane, piperidine (NH), tetrahydropyran (O), cycloheptane, tetralin, and various fused bicyclic/tricyclic aromatic systems including dibenzosuberane-type structures]

These examples illustrate but do not limit the scope of the present invention.

The peptides of the formula I are composed of L-amino acids but they may contain one or more D-amino acids.

The new compounds may be present as salts with physiologically tolerated acids such as: hydrochloric acid, citric acid, tartaric acid, lactic acid, phosphoric acid, methanesulfonic acid, acetic acid, formic acid, maleic acid, fumaric acid, malic acid, succinic acid, malonic acid, sulfuric acid, L-glutamic acid, L-aspartic acid, pyruvic acid, mucic acid, benzoic acid, glucuronic acid, oxalic acid, ascorbic acid and acetylglycine.

Particularly preferred compounds are those where the radicals have the following meanings:

$R_A$: hydrogen, methyl, ethyl, propyl, isopropyl, cyclopropyl, 2,2,2-trifluoroethyl, 2-fluoroethyl;

$R^1_A$: hydrogen, methyl, ethyl, propyl, isopropyl, cyclopropyl, 2,2,2-trifluoroethyl, 2-fluoroethyl;

$R^2_A$: hydrogen, methyl, ethyl, propyl, isopropyl, butyl, tert-butyl, isobutyl, cyclopropyl, cyclobutyl, 2,2,2-trifluoroethyl, 2-fluoroethyl;

T an NH group and $R^1_B$ hydrogen, $R^2_B$ cyclopropyl, ethyl, isopropyl, butyl, tert-butyl, sec.-butyl, methoxymethyl, 1-methoxyethyl, 1-methylvinyl;

or $R^1_B$ and $R^2_B$ together an isopropylidene group, or

T an oxygen atom and $R^1_B$ hydrogen;

$R^2_B$ methyl, ethyl, propyl, isopropyl, butyl, sec-butyl, tert-butyl, isobutyl, pentyl, hexyl;

$R_D$: hydrogen, methyl, ethyl, propyl, isopropyl, cyclopropyl, 2,2,2-trifluoroethyl, 2-fluoroethyl;

$R^1_D$ hydrogen;

$R^2_D$ methyl, ethyl, propyl, isopropyl, butyl, sec-butyl, tert-butyl, isobutyl, pentyl, 3-methylbutyl, 2,3-dimethylpropyl, cyclopropyl, cyclobutyl, methoxymethyl, 1-methoxyethyl, 1-methylvinyl, or E is a substituted azetidinyl, pyrrolidinyl or piperidinyl radical of the following formula:

[structures of azetidinyl, pyrrolidinyl, piperidinyl and related heterocyclic radicals with substituents $R^1_E$, $R^2_E$, $R^3_E$, $R^4_E$, $R^5_E$ and $R^1_D$]

where
$R^1_E$ is hydrogen, $C_{1-3}$-alkyl which can be substituted by 1 to 3 fluorine atoms or cyclopropyl which can be substituted by 1 to 3 fluorine atoms, $R^2_E$ and $R^3_E$ are, independently of one another, a hydrogen atom or a methyl group;

$R^4_E$ is hydrogen, a hydroxyl group, a methoxy or ethoxy radical or a fluorine atom;

$R^5_E$ is hydrogen or fluorine or

E is a substituted aminocyclopentylcarbonyl radical of the following formula:

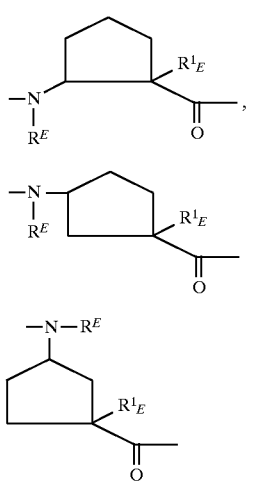

where
$R^E$ is hydrogen methyl or ethyl, and
$R^1_E$ is $C_{1-3}$-alkyl which can be atoms or cyclopropyl which can be substituted by 1 to 3 fluorine atoms, F has the meanings stated for E or is a radical of the formula

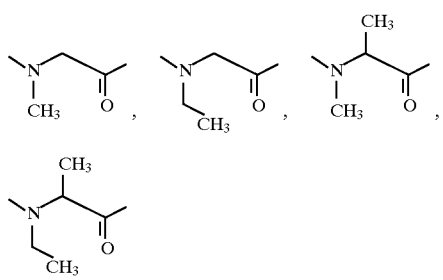

Very particularly preferred peptides of the formula $$A\text{—}B\text{—}D\text{—}E\text{—}F\text{—}L \qquad (I),$$

are those where the radicals have the following meanings:

A is

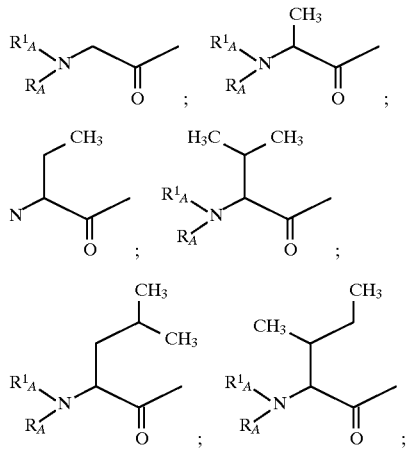

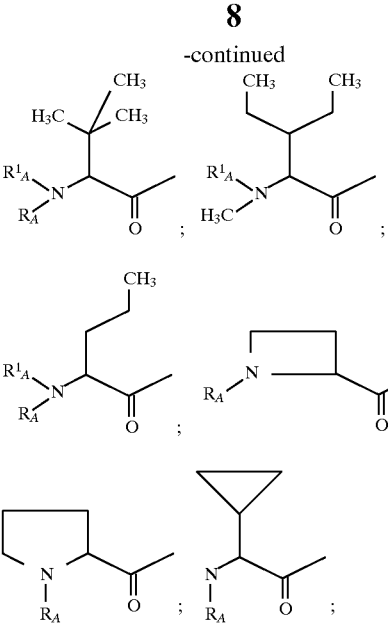

where $R_A$ and $R^1_A$ have the abovementioned meanings;

B is 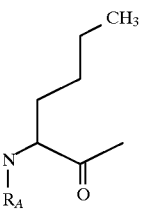

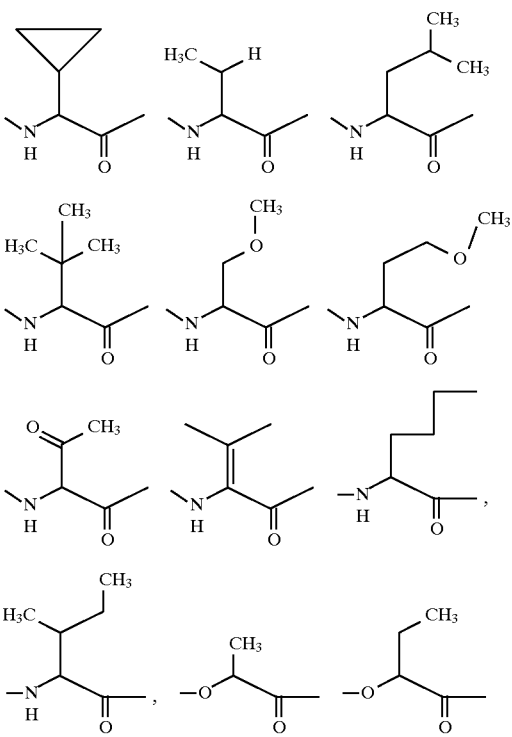

-continued
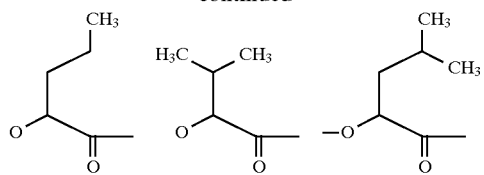
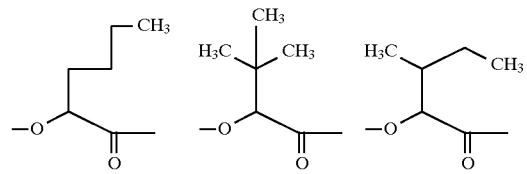
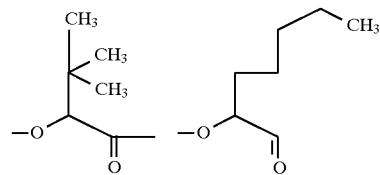
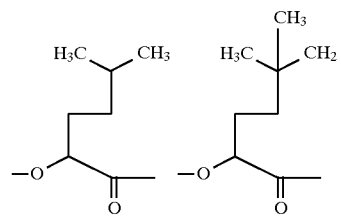
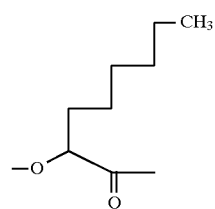
D is
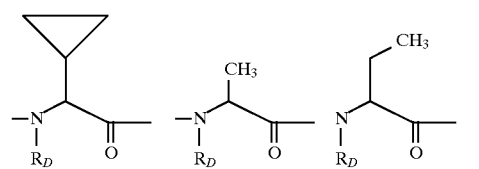
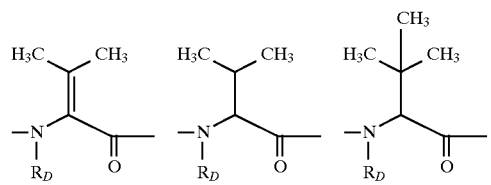
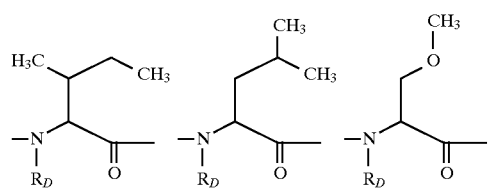
-continued
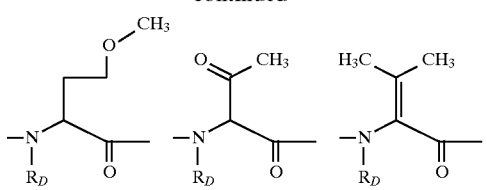
where $R_D$ has the abovementioned meanings,
E is
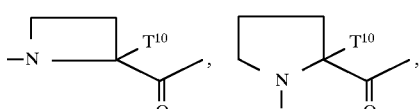
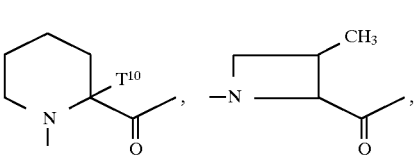
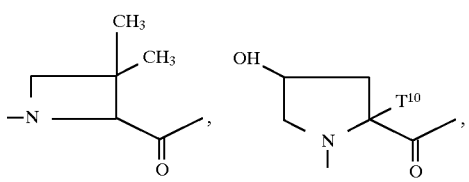
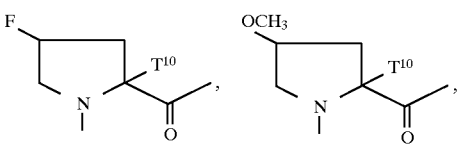
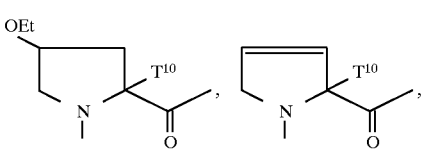
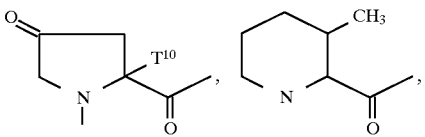
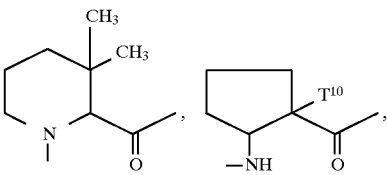
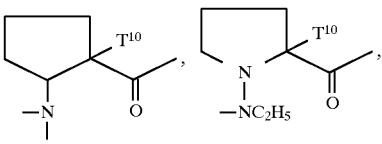

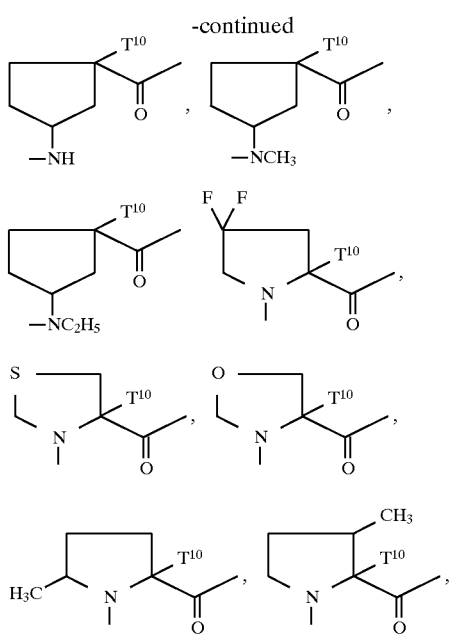

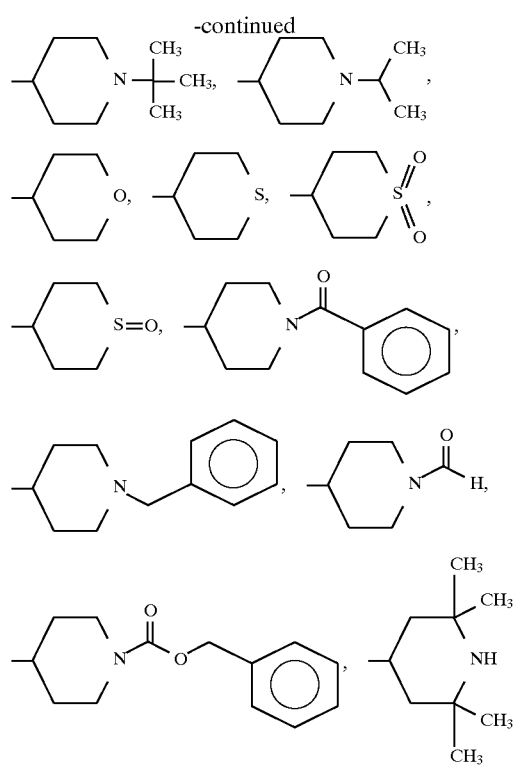

$T^{10}$ is hydrogen, $C_{1-3}$-alkyl which can be substituted by 1 to 3 fluorine atoms or cyclopropyl which can be substituted by 1 to 3 fluorine atoms.

F has the meanings stated for E.

The radical L is preferably a radical of the formula —O—$R_L$ where the radical $R_L$ is preferably $C_3$–$C_{16}$-alkyl such as pentyl, hexyl, heptyl, octyl, nonyl, decyl, undecyl, dodecyl, tridecyl, tetradecyl, pentadecyl, hexadecyl, heptadecyl, octadecyl, 1-methylethyl, 2-methylbutyl, 3-methylbutyl, 2-methylpropyl, 2,2-dimethylbutyl, 2,3-dimethylbutyl, 3,3-dimethylbutyl, 4-methylpentyl, 4,4-dimethylpentyl, 3-pentyl, 4-heptyl, 2,2,2-trifluoroethyl, 1-fluoroethyl, 2,2-difluoroethyl, 1,3-difluoro-2-propyl $C_3$–$C_{10}$-cycloalkyl, such as cyclopropyl, cyclobutyl, cyclopentyl, cyclohexyl, cycloheptyl, cyclooctyl, cyclononyl, cyclodecyl.

Methyl-, ethyl- or propyl-($C_3$–$C_{10}$)-cycloalkyl; methyladamantyl; $C_2$–$C_{16}$-alkenyl, such as 2-propenyl, 3-butenyl, 2-butenyl, 2-methyl-2-propenyl, 2-pentenyl, 3-methyl-2-propenyl, 3-pentenyl, 4-pentenyl, 2-methyl-2-butenyl, 3,7-dimethyl-2,6-octadienyl, 3,7,11-trimethyldodeca-2,6,10-trienyl, 3,7,11,15-tetramethylhexadeca-2,6,10,14-tetraenyl;

a saturated heterocycle such as

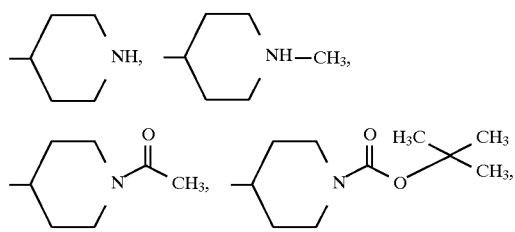

2-methoxyethyl, 2-(2-methoxy-ethoxy)ethyl, 2-[2-(2-methoxy-ethoxy)ethoxy]ethyl, 2-{2-[2-(2-methoxy-ethoxy)ethoxy]ethoxy}ethyl;

$R_L$ is also preferably radicals such as aryl, methylaryl, ethylaryl, propylaryl, where aryl can be substituted or unsubstituted.

Aryl is preferably a phenyl or naphthyl radical of the formula

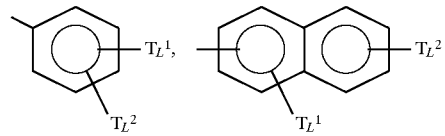

where suitable substituents $T_L^1$ and $T_L^2$ are independently of one another, the following radicals (with the proviso that $R_L$ is not phenyl):

H, Cl, F, Br, $C_{1-4}$-alkyl, $C_{1-4}$-alkoxy, trifluoromethyl, trifluoromethoxy, nitro, cyano, dioxymethylene or -ethylene, $C_{1-7}$-alkoxycarbonyl, $C_{1-7}$-alkylsulfonyl, amino or $C_{1-7}$-dialkylamino, in which the alkyl groups can together form a heterocycle; or methylhetaryl, ethylhetaryl, propylhetaryl, where hetaryl can be substituted or unsubstituted.

Hetaryl is preferably:

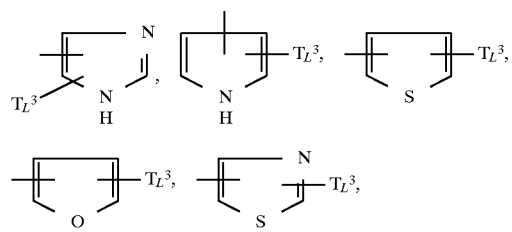

-continued

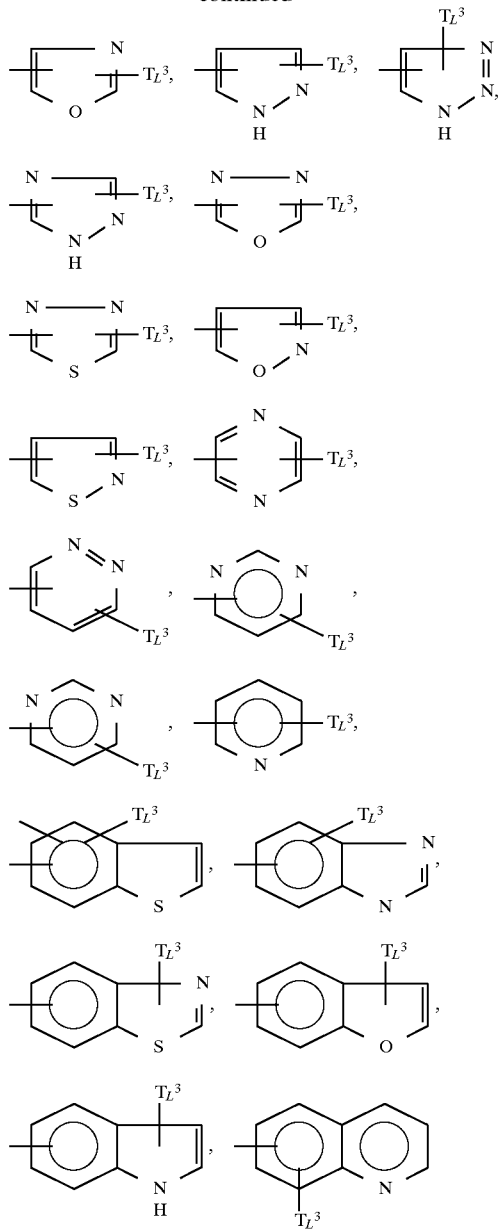

with $T_L^3$=H, OH, $C_{1-4}$-alkyl, phenyl, a straight-chain or branched $C_{1-5}$-alkylcarbonyl-, $C_{1-10}$-alkoxy group such as:

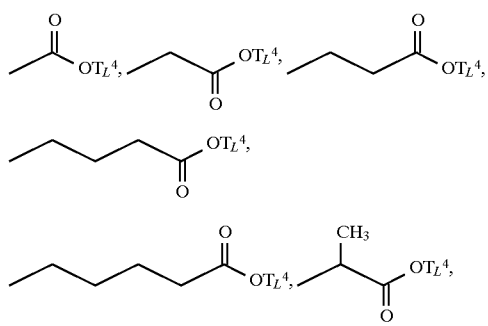

-continued

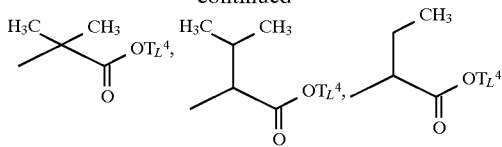

with $T_L^4$=$C_{1-4}$-alkyl; a radical of the formula

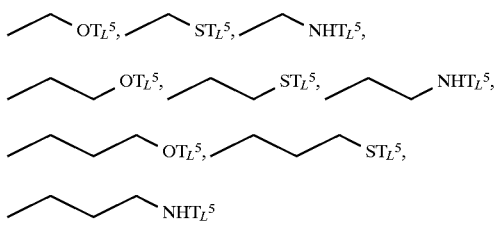

with $T_L^5$=H, $C_{1-4}$-alkyl, $C_{1-6}$-cycloalkyl,

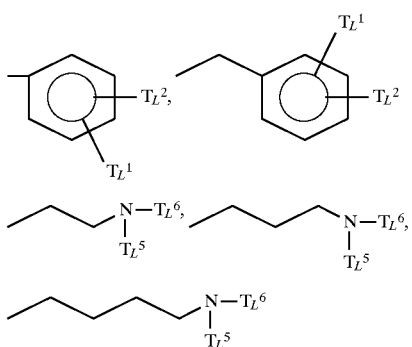

with $T_L^6$ having the meanings stated for $T_L^5$ and additionally being $C_{1-4}$-acyl, benzoyl, tert-butyloxycarbonyl, benzyloxycarbonyl,

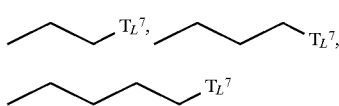

with $T_L^7$=CHO, NHCHO, NHNHCHO, or a radical of the formula

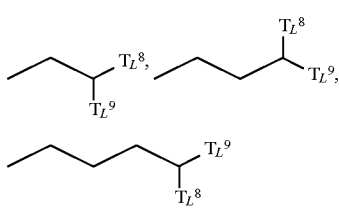

with $T_L^8$, $T_L^9$=$OCH_3$, $OC_2H_5$, $SCH_3$, $SC_2H_5$, or $T_L^8$ and $T_L^9$ together with the C atom they are connected to form a cyclic system of the formula

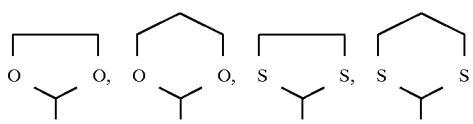

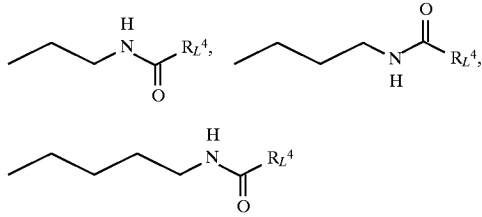

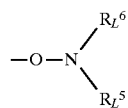

with $R_L^4$ being a polyethylene glycol ester of the formula —O—(CH$_2$CH$_2$O)$_{hL}$—CH$_3$ with hL being a number from 40 to 90.

Another group includes substances where L is a hydroxylamine residue of the formula $$-O-N\begin{matrix}R_L^6\\R_L^5\end{matrix} \qquad (V_L)$$

where $R_L^5$ is preferably

- hydrogen, methyl, ethyl, propyl, butyl, tert-butyl, pentyl, hexyl, heptyl, octyl, 2-methylbutyl, 3-methylbutyl, 2-methylethyl, 2-methylpropyl, 2,2-dimethylbutyl, 2,3-dimethylbutyl, 3,3-dimethylbutyl, 4-methylpentyl, 4,4-dimethylpentyl, 2,2,2-trifluoroethyl, 1-fluoroethyl, 2,2-difluoroethyl, C$_{3-8}$-cycloalkyl, such as cyclopropyl, cyclobutyl, cyclopentyl, cyclohexyl, cycloheptyl, cyclooctyl, cyclononyl, cyclodecyl; methyl-, ethyl-, propyl-, butyl-C$_{3-10}$-cycloalkyl,
- a substituted or unsubstituted aryl or hetaryl radical or an C$_{1-4}$-alkyl-aryl- or -hetaryl with the meanings stated for $R_L$; and $R_L^6$ is Z methyl, ethyl, propyl, butyl, tert-butyl, pentyl, hexyl, heptyl, octyl, 2-methylbutyl, 3-methylbutyl, 2-methylethyl, 2-methylpropyl, 2,2-dimethylbutyl, 2,3-dimethylbutyl, 3,3-dimethylbutyl, 4-methylpentyl, 4,4-dimethylpentyl, 2,2,2-trifluoroethyl, 1-fluoroethyl, 2,2-difluoroethyl, C$_{3-8}$-cycloalkyl, such as cyclopropyl, cyclobutyl, cyclopentyl, cyclohexyl, cycloheptyl, cyclooctyl, cyclononyl, cyclodecyl; methyl-, ethyl-, propyl-, butyl-C$_{3-10}$-cycloalkyl, or $R_L^5$—N—$R_L^6$ form a cyclic system with the following formula:

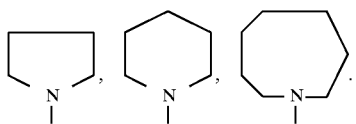

Another group of preferred compounds includes oxime esters of the formula

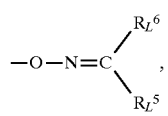

where $R_L^5$ and $R_L^6$ have the abovementioned meanings, or

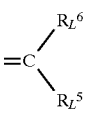

form a cyclic system of the following formula:

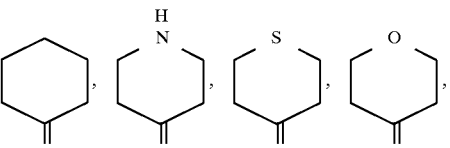

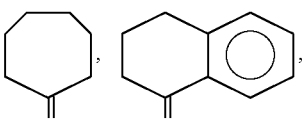

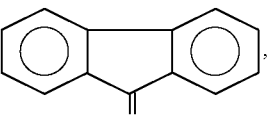

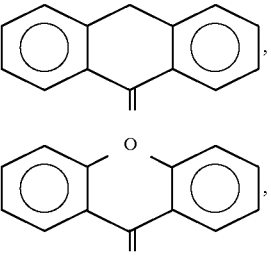

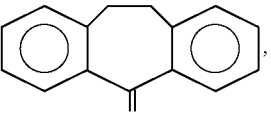

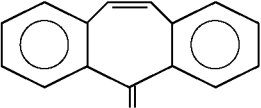

In general,

C$_{1-4}$-alkyl is methyl, ethyl, propyl, 2-methylethyl, butyl, tertbutyl, 3-methylpropyl;

C$_{1-4}$-alkoxy is methoxy, ethoxy, propoxy, butoxy, tert-butoxy, 2-methylethoxy, 3-methylpropoxy;

C$_{1-4}$-alkylsulfonyl is —SO$_2$CH$_3$, —SO$_2$C$_2$H$_5$, —SO$_2$C$_3$H$_7$, —SO$_2$C$_4$H$_9$, —SO$_2$C$_5$H$_{11}$, —SO$_2$C$_6$H$_{13}$, —SO$_2$C$_7$H$_{15}$;

a C$_{1-7}$-dialkylamino group, where the alkyl radicals can form a common heterocycle is

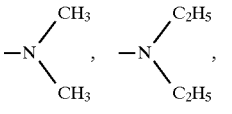

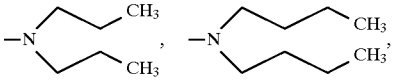

-continued

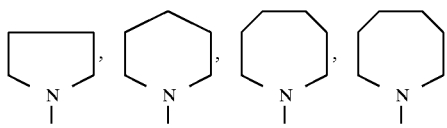

C$_{3-8}$-cycloalkyl is cyclopropyl, cyclobutyl, cyclopentyl, cyclohexyl, cycloheptyl, cyclooctyl.

The novel compounds can be prepared by known methods of peptide chemistry. Thus, the peptides can be assembled sequentially from amino acids or by linking suitable small peptide fragments. In the sequential assemblage, starting at the C terminus the peptide chain is extended stepwise by one amino acid each time. In fragment coupling it is possible to link together fragments of different lengths, and the fragments in turn can be obtained by sequential assemblage from amino acids or themselves by fragment coupling.

Both in the sequential assemblage and in the fragment coupling it is necessary to link the units by forming an amide, ester or hydroxylamine linkage. Enzymatic and chemical methods are suitable for this.

Chemical methods for forming the amide linkage are described in detail by Müller, Methoden der organischen Chemie Vol. XV/2, pp 1 to 364, Thieme Verlag, Stuttgart, 1974; Stewart, Young, Solid Phase Peptide Synthesis, pp 31 to 34, 71 to 82, Pierce Chemical Company, Rockford, 1984; Bodanszky, Klausner, Ondetti, Peptide Synthesis, pp 85 to 128, John Wiley & Sons, New York, 1976 and other standard works on peptide chemistry. Particular preference is given to the azide method, the symmetric and mixed anhydride method, in situ generated or preformed active esters, the use of urethane protected N-carboxy anhydrides of amino acids and the formation of the amide linkage using coupling reagents (activators, especially dicyclohexylcarbodiimide (DCC), diisopropylcarbodiimide (DIC), 1-ethoxycarbonyl-2-ethoxy-1,2-dihydroquinoline (EEDQ), 1-ethyl-3-(3-dimethylaminopropyl)carbodiimide hydrochloride (EDCI), n-propanephosphonic anhydride (PPA), N,N-bis(2-oxo-3-oxazolidinyl)-midophosphoryl chloride (BOP-Cl), bromo-tris-pyrrolidinophosphonium hexa-fluorophosphate (PyBrop), diphenylphosphoryl azide (DPPA), Castro's reagent (BOP, PyBop), O-benzotriazolyl-N,N,N',N'-tetramethyluronium salts (HBTU), diethylphosphoryl cyanide (DEPCN), 2,5-diphenyl-2,3-dihydro-3-oxo-4-hydroxythiophene dioxide (Steglich's reagent; HOTDO) and 1,1'-carbonyldiimidazole (CDI) 7-azabenzotriazolyl-N,N,N',N'-tetramethyluronium salts (HATU: described in THL Vol. 35, No. 33, 5981–5984). The coupling reagents can be employed alone or in combination with additives such as N,N-dimethyl-4-aminopyridine (DMAP), N-hydroxybenzotriazole (HOBt), 1-hydroxy-7-azabenzotriazol (HOAt), N-hydroxybenzotriazine (HOOBt), N-hydroxysuccinimide (HOSu) or 2-hydroxypyridine.

Formation of the ester or hydroxylamine linkage can be achieved by coupling a suitable amino acid or peptide derivative with a hydroxy- or hydroxylamino compound in the presence of coupling reagent and a base. Particular preference is given to the methods and coupling reagents already described for the formation of the amide linkage. Suitable bases are organic amines, such as N,N-dimethylaminopyridine (DMAP), pyridine, N-methylmorpholine, triethylamine.

Whereas it is normally possible to dispense with protective groups in enzymatic peptide synthesis, reversible protection of reactive groups not involved in formation of the amide linkage is necessary for both reactants in chemical synthesis. Three conventional protective group techniques are preferred for the chemical peptide synthesis: the benzyloxycarbonyl (Z), the t-butoxycarbonyl (Boc) and the 9-fluorenylmethoxycarbonyl (Fmoc) techniques. Identified in each case is the protective group on the α-amino group of the chain-extending unit. A detailed review of amino-acid protective groups is given by Müller, Methoden der organischen Chemie Vol. XV/1, pp 20 to 906, Thieme Verlag, Stuttgart, 1974. The units employed for assembling the peptide chain can be reacted in solution, in suspension or by a method similar to that described by Merrifield in J. Amer. Chem. Soc. 85 (1963) 2149. Particularly preferred methods are those in which peptides are assembled sequentially or by fragment coupling using the Z, Boc or Fmoc protective group technique, with one of the reactants in the said Merrifield technique being bonded to an insoluble polymeric support (also called resin hereinafter). This typically entails the peptide being assembled sequentially on the polymeric support using the Boc or Fmoc protective group technique, the growing peptide chain being covalently bonded at the C terminus to the insoluble resin particles (cf. FIGS. 1 and 2). This procedure makes it possible to remove reagents and byproducts by filtration, and thus recrystallization of intermediates is unnecessary.

The protected amino acids can be linked to any suitable polymers, which merely have to be insoluble in the solvents used and to have a stable physical form which makes filtration easy. The polymer must contain a functional group to which the first protected amino acid can be firmly attached by a covalent bond. Suitable for this purpose are a wide variety of polymers, eg. cellulose, polyvinyl alcohol, polymethacrylate, sulfonated polystyrene, chloromethylated styrene/divinylbenzene copolymer (Merrifield resin), 4-methylbenzhydrylamine resin (MBHA-resin), phenylacetamidomethyl-resin (Pam-resin), p-benzyloxybenzyl-alcohol-resin, benzhydryl-amine-resin (BHA-resin), 4-(hydroxymethyl)benzoyloxy-methyl-resin, the resin of Breipohl et al. (Tetrahedron Letters 28 (1987) 565; supplied by BACHEM), 4-(2,4-dimethoxyphenylaminomethyl) phenoxy-resin (supplied by Novabiochem) or o-chlorotrityl-resin (supplied by Biohellas).

Suitable for peptide synthesis in solution are all solvents which are inert under the reaction conditions, especially water, N,N-dimethylformamide (DMF), dimethyl sulfoxide (DMSO), acetonitrile, dichloromethane (DCM), 1,4-dioxane, tetrahydrofuran (THF), N-methyl-2-pyrrolidone (NMP) and mixtures of the said solvents. Peptide synthesis on the polymeric support can be carried out in all inert organic solvents in which the amino-acid derivatives used are soluble; however, preferred solvents additionally have resin-swelling properties, such as DMF, DCM, NMP, acetonitrile and DMSO, and mixtures of these solvents. After synthesis is complete, the peptide is cleaved off the polymeric support. The conditions under which cleavage off the various resin types is possible are disclosed in the literature. The cleavage reactions most commonly used are acid- and palladium-catalyzed, especially cleavage in liquid anhydrous hydrogen fluoride, in anhydrous trifluoromethanesulfonic acid, in dilute or concentrated trifluoroacetic acid, palladium-catalyzed cleavage in THF or THF-DCM mixtures in the presence of a weak base such as morpholine or cleavage in acetic acid/dichloromethane/trifluoroethanol mixtures. Depending on the chosen protective groups, these may be retained or likewise cleaved off under the cleavage conditions. Partial deprotection of the peptide may also be worthwhile when certain derivatization reactions are to be carried out. Peptides dialkylated at the N-terminus can be prepared either by coupling of the appropriate N,N-dialkylamino acids in solution or on the polymeric support or by reductive alkylation of the resin-bound peptide in DMF/ 1% acetic acid with NaCNBH$_3$ and the appropriate aldehydes.

The compounds of this invention may be used to inhibit or otherwise treat solid tumors (e.g. tumors of the lung, breast, colon, prostate, bladder, rectum, or endometrial tumors) or hematological malignancies (e.g. leucemias, lymphomas) by administration of the compound to the mammal. Administration may be by any of the means which are conventional for pharmaceutical, preferably oncological, agents, including oral and parenteral means such as subcutaneously, intravenously, intramuscularly and intraperitoneally. The compounds may be administered alone or in the form of pharmaceutical compositions containing a compound of formula I together with a pharmaceutically accepted carrier appropriate for the desired route of administration. Such pharmaceutical compositions may be combination products, i.e., may also contain other therapeutically active ingredients.

The dosage to be administered to the mammal will contain an effective tumor-inhibiting amount of active ingredient which will depend upon conventional factors including the biological activity of the particular compound employed; the means of administration; the age, health and body weight of the recipient; the nature and extent of the symptoms; the frequency of treatment; the administration of other therapies; and the effect desired. A typical daily dose will be about 0.05 to 250 milligrams per kilogram of body weight on oral administration and about 0.05 to 100 milligrams per kilogram of body weight on parenteral administration.

The novel compounds can be administered in conventional solid or liquid pharmaceutical administration forms, eg. uncoated or (film-)coated tablets, capsules, powders, granules, suppositories or solutions. These are produced in a conventional manner. The active substances can for this purpose be processed with conventional pharmaceutical aids such as tablet binders, fillers, preservatives, tablet disintegrants, flow regulators, plasticizers, wetting agents, dispersants, emulsifiers, solvents, sustained release compositions, antioxidants and/or propellant gases (cf. H. Sucker et al.: Pharmazeutische Technologie, Thieme-Verlag, Stuttgart, 1978). The administration forms obtained in this way normally contain 1–90% by weight of the active substance.

The following examples are intended to illustrate the invention. The proteinogenous amino acids are abbreviated in the examples using the known three-letter code. Other meanings are: TFA=trifluoroacetic acid, Ac=acetic acid, Bu=butyl, Et=ethyl, Me=methyl, Bzl=benzyl.

A. General Procedures

I. The peptides claimed in claim 1 are either synthesized by classical solution synthesis using standard Z- and Boc-methodology as described above or by standard methods of solid-phase synthesis on a completely automatic model 431A synthesizer supplied by APPLIED BIOSYSTEMS. The apparatus uses different synthetic cycles for the Boc and Fmoc protective group techniques.

a) Synthetic cycle for the Boc protective group technique
1. 30% trifluoroacetic acid in DCM 1×3 min
2. 50% trifluoroacetic acid in DCM 1×1 min
3. DCM washing 5×1 min
4. 5% diisopropylethylamine in DCM 1×1 min
5. 5% diisopropylethylamine in NMP 1×1 min
6. NMP washing 5×1 min
7. Addition of preactivated protected amino acid (activation with 1 equivalent of DCC and 1 equivalent of HOBt in NMP/DCM); Peptide coupling (1st part) 1×30 min
8. Addition of DMSO to the reaction mixture until it contains 20% DMSO by volume
9. Peptide coupling (2nd part) 1×16 min
10. Addition of 3.8 equivalents of diisopropylethylamine to the reaction mixture
11. Peptide coupling (3rd part) 1×7 min
12. DCM washing 3×1 min
13. if conversion is incomplete, repetition of coupling (back to 5.)
14. 10% acetic anhydride, 5% diisopropylethylamine in DCM 1×2 min
15. 10% acetic anhydride in DCM 1×4 min
16. DCM washing 4×1 min
17. back to 1.

BOP-Cl and PyBrop were used as reagents for coupling of the amino acid following N-methylamino acids. The reaction times were correspondingly increased. In solution synthesis, the use of either Boc-protected amino acid NCAs (N-tert.-butyloxycarbonyl-amino acid-N-carboxy-anhydrides) or Z-protected amino acid NCAs (N-benzyloxycarbonyl-amino acid-N-carboxy-anhydrides) respectively is most advantageous for this type of coupling.

b) Synthetic cycle for the Fmoc protective group technique
1. DMF washing 1×1 min
2. 20% piperidine in DMF 1×4 min
3. 20% piperidine in DMF 1×16 min
4. DMF washing 5×1 min
5. Addition of the preactivated protected amino acid (activation by 1 equivalent of TBTU and 1.5 equivalent of DIPEA in DMF); Peptide coupling 1×61 min
6. DMF washing 3×1 min
7. if conversion is incomplete, repetition of coupling (back to 5.)
8. 10% acetic anhydride in DMF 1×8 min
9. DMF washing 3×1 min
10. back to 2.

BOP-Cl and PyBrop were used as reagents for coupling on the amino acid following the N-methylamino acids. The reaction times were correspondingly increased.

II. Reductive alkylation of the N terminus

The peptide-resin prepared as in AIa or AIb was deprotected at the N terminus (steps 2–4 in AIb or 1–6 in AIa) and then reacted with a 3-fold molar excess of aldehyde or ketone in DMF/1% acetic acid with addition of 3 equivalents of NaCNBH$_3$. After reaction was complete (negative Kaiser test) the resin was washed several times with water, isopropanol, DMF and dichloromethane.

III. Workup of the peptide-resins obtained as in Ia and II

The peptide-resin was dried under reduced pressure and transferred into a reaction vessel of a TEFLON HF apparatus (supplied by PENINSULA). Addition of a scavenger, preferably anisole (1 ml/g of resin), and in the case of tryptophan-containing peptides of a thiol to remove the indolic formyl group, preferably ethane-dithiol (0.5 ml/g of resin), was followed by condensing in hydrogen fluoride (10 ml/g of resin) while cooling with liquid N$_2$. The mixture was left to warm to 0° C. and stirred at this temperature for 45 min. The hydrogen fluoride was then stripped off under reduced pressure, and the residue was washed with ethyl acetate in order to remove remaining scavenger. The peptide was extracted with 30% strength acetic acid and filtered, and the filtrate was lyophilized.

IV. Work-up of the peptide-resins obtained as in Ib and II

The peptide-resin was dried under reduced pressure and then subjected to one of the following cleavage procedures, depending on the amino-acid composition (Wade, Tregear, Howard Florey Fmoc Workshop Manual, Melbourne 1985).

| | Cleavage conditions | | |
|---|---|---|---|
| | TFA | Scavenger | Reaction time |
| 1 | 95% | 5% H₂O | 1.5 h |
| 2 | 95% | 5% ethanedithiol/anisol (1:3) | 1.5 h |

The suspension of the peptide-resin in the suitable TFA mixture was stirred at room temperature for the stated time and then the resin was filtered off and washed with TFA and DCM. The filtrate and the washings were concentrated, and the peptide was precipitated by addition of diethyl ether. After cooling in an ice bath, the precipitate was filtered off, taken up in 30% acetic acid and lyophilized.

V. When an o-chlorotrityl-resin (supplied by Biohellas) is used, the suspension of the peptide-resin in an acetic acid/trifluoroethanol/dichloromethane mixture (1:1:3) is stirred at room temperature for 1 h. The resin is then filtered off with suction and thoroughly washed with the cleavage solution. The combined filtrates are concentrated in acuo and treated with water. The precipitated solid is removed by filtration or centrifugation, washed with diethyl ether and dried under reduced pressure.

FIG. 1: The Boc protective group technique on a polymeric support

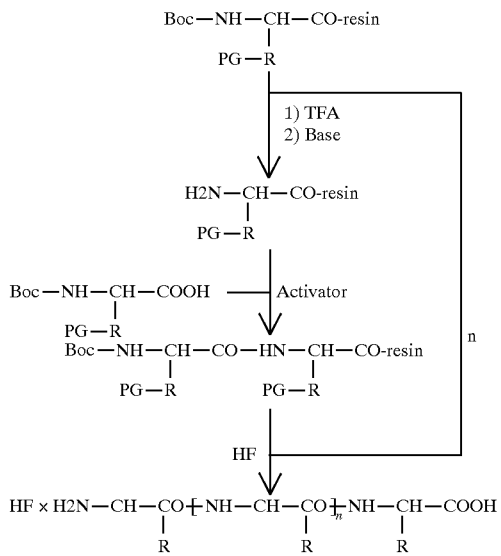

Boc=t-butyloxycarbonyl protective group

PG=side-chain protective group

R=amino-acid side chain

FIG. 2: The Fmoc protective group technique on a polymeric support

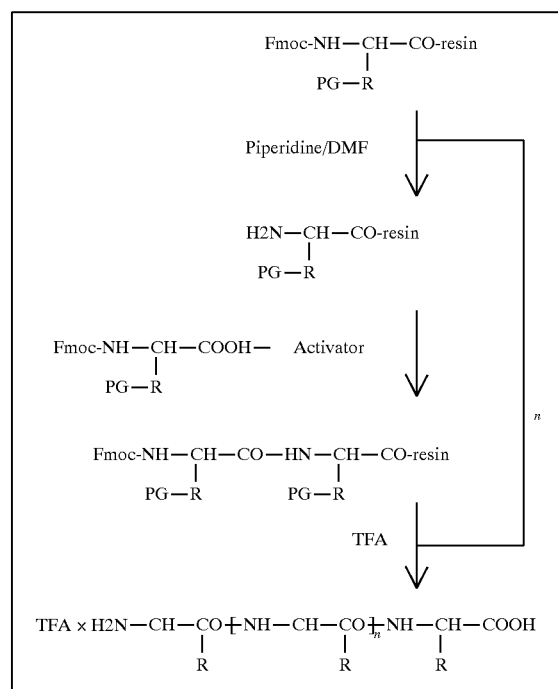

Fmoc=9-fluorenylmethyloxycarbonyl protective group

PG=side-chain protective group

R=amino-acid side chain

VI. Formation of the ester or hydroxylamino linkage

A suitable amino acid or peptide derivative was dissolved in THF, DMF or a mixture of both solvents. After cooling to a temperature between −20° C. and −10° C. 1.5 equivalents of EDCI and 1.5 equivalents of DMAP were added, after stirring for about 1 h 1.5 eq. of the hydroxy- or or hydroxylamino compound was added. The reaction was stirred for 2 h at about 0° C., then for about 24 h at room temperature. After the reaction was complete the mixture was poured into a saturated NaCl-solution and extracted several times with ethylacetate or dichloromethane. The organic phases were combined and evaporated.

VII: Purification and characterization of the peptides

Purification was carried out by gel chromatography (SEPHADEX G-10, G-15/10% HOAc, SEPHADEX LH20/MeOH) with or without subsequent medium pressure chromatography (MPLC) (stationary phase: HD-SIL C-18, 20–45μ, 100 Å; mobile phase: gradient with A=0.1% TFA/MeOH, B=0.1% TFA/H₂O).

The purity of the resulting products was determined by analytical HPLC (stationary phase: 100 2.1 mm VYDAC C-18, 5 1, 300 Å; mobile phase: CH₃CN/H₂O gradient, buffered with 0.1% TFA, 40° C.). Characterization was fast atom bombardment mass spectroscopy.

B. Synthesis of Building Blocks

1. Me₂Val-Val-MeVal-Pro-Pro-OMe×HCl a) 234 g (0.463 mol) of Me₂Val-Val-MeVal-Pro-OMe× HCl were dissolved in a mixture of 2.3 l of toluene and 150 ml of methanol, then 47.7 g (1.157 mol) of NaOH were added and the mixture was stirred at room temperature for about 20 h.

It was then concentrated, 500 ml of CH₂Cl₂ were added to the residue, and the mixture was again concentrated.

b) The crude product obtained in this way was suspended in 2.5 l of CH₂Cl₂ and, at +10° C., 178 g (1.76 mol) of triethylamine and 85.5 g (0.71 mol) of pivaloyl chloride were added dropwise. The mixture was stirred at 5°–10° C. for about 1 h and then 77.6 g of H-Pro-OMe×HCl were introduced in portions and the mixture was stirred at 10° C. for 2 h and then at room temperature overnight.

For workup, the mixture was concentrated, the residue was partitioned between 850 ml of $H_2O$ and 1.1 l of toluene, and the pH was adjusted to about 1.5 with concentrated HCl while stirring.

After separating the phases, 1 l of $CH_2Cl_2$ was added to the aqueous phase, the pH was adjusted to 9 with concentrated sodium hydroxide solution, the phases were separated and the aqueous phase was re-extracted. Concentration of the combined organic phases resulted in about 285 g of residue.

c) The resulting residue was dissolved in 1.6 l of isopropanol and, at 40° C., 64 g of isopropanolic HCl (29%) were added, and the mixture was allowed to cool to room temperature with stirring. After about 2 h, the precipitate was filtered off, washed with isopropanol and methyl tert-butyl ether and dried at 50° C. This resulted in 222 g of pentapeptide with a purity of 98.8% (according to HPLC).

2. $Me_2$Val-Val-MeVal-Pro-Pro—OH×HCl 222 g (0.367 Mol) of $Me_2$Val-Val-MeVal-Pro-Pro-OMe× HCl were dissolved in 700 ml of $H_2O$, and 38 g (0.94 mol) of NaOH were added.

After the reaction was complete, the mixture was acidified by adding 61.7 g of concentrated HCl and was then concentrated. The crystalline residue was mixed with 500 ml of $CH_3OH$, again concentrated and then stirred with 1 l of acetone at 50° C. The precipitate was filtered off with suction and dried and then dissolved in 1.6 l of acetone and, while stirring, 47.5 g of isopropanol/HCl (30%) were added and the mixture was stirred at room temperature for 2 h. The precipitate obtained in this way was again filtered off with suction, washed with acetone and dried at 50° C.

This resulted in 191.2 g of pure product (99.9% according to HPLC). Melting point: 242° to 244° C.

C. Specific Procedures

General method 1 eq of peptide acid was dissolved together with 1 to 2 eq of the appropriate nucleophile (alcohol, hydroxylamine, oxime) in DMF/THF and, at –10° C., 1 to 2 eq each of DMAP, EDC×HCl and HOBt were added; the mixture was subsequently stirred at –10° C. and then at room temperature. For workup, aqueous NaCl solution is added to the mixture and it is extracted with suitable organic solvents such as $CH_2Cl_2$, or the reaction mixture is concentrated directly. The crude product obtained in this way can then be purified by chromatography on silica gel ($CH_2Cl_2/CH_3OH$ as eluent) or MPLC on RP silica gel ($CH_3CN/H_2O$+TFA).

EXAMPLE

I-1 $Me_2$Val-Val-MeVal-Pro-Pro cyclohexyl ester 1.2 g (2 mmol) of $Me_2$Val-Val-MeVal-Pro-Pro—OH×HCl and 0.27 g (2.7 mmol) of cyclohexanol were dissolved in 50 ml of 4:1 DMF/THF and then, at –10° C., 0.5 g (4.1 mmol) DMAP, 0.43 g (2.2 mmol) of EDC×HCl and 0.34 g (2.2 mmol) of HOBt were successively added. The mixture was then stirred at –10° C. for 2 h and at room temperature overnight. For workup, the reaction mixture was poured into saturated NaCl solution and thoroughly extracted with ethyl acetate. The residue remaining after the combined organic phases had been dried and concentrated was purified on silica gel (eluent $CH_2Cl_2/CH_3OH$ 2%).

This resulted in 0.26 g of the ester as white foam. FAB-MS: 634.5 (M+H$^+$).

The following were prepared in a similar way:

I-20 $Me_2$Val-Val-MeVal-Pro-Pro-dodecyl ester FAB-MS: 720.5 (M+H$^+$)

I-26 $Me_2$Val-Val-MeVal-Pro-Pro-octadecyl ester FAB-MS: 804.5 (M+H$^+$)

I-89 $Me_2$Val-Val-MeVal-Pro-Pro 2-(tert-butyloxycarbonylamino)ethyl ester FAB-MS: 695.5 (M+H$^+$)

I-14 $Me_2$Val-Val-MeVal-Pro-Pro-hexyl ester FAB-MS: 636.5 (M+H$^+$)

I-2 $Me_2$Val-Val-MeVal-Pro-Pro-cyclopentyl ester FAB-MS: 620.5 (M+H$^+$)

I-58 $Me_2$Val-Val-MeVal-Pro-Pro-trans-3-methyl-2-butenyl ester FAB-MS: 620 (M+H$^+$)

I-59 $Me_2$Val-Val-MeVal-Pro-Pro-trans-3,7-dimethyl-2,6-octadienyl ester FAB-MS: 688.5 (M+H$^+$)

I-49 $Me_2$Val-Val-MeVal-Pro-Pro-1-adamantanylmethyl ester FAB-MS: 700.4 (M+H$^+$)

I-35 $M_2$Val-Val-MeVal-Pro-Pro-3-pentyl ester FAB-MS: 630.5 (M+H$^+$)

I-64 $M_2$Val-Val-MeVal-Pro-Pro-N-methyl-4-piperidyl ester FAB-MS: 649.4 (M+H$^+$)

I-62 $Me_2$Val-Val-MeVal-Pro-Pro-1,3-difluoro-2-propyl ester FAB-MS: 630.5 (M+H$^+$)

I-74 $Me_2$Val-Val-MeVal-Pro-Pro-2-hydroxyethyl ester FAB-MS: 654 (M+H$^+$)

I-76 $Me_2$Val-Val-MeVal-Pro-Pro-2-(methoxyethoxy)ethyl ester FAB-MS: 654 (M+H$^+$)

I-78 $Me_2$Val-Val-MeVal-Pro-Pro-2-(2-butoxyethoxy)ethyl ester FAB-MS: 696.5 (M+H$^+$)

I-79 $Me_2$Val-Val-MeVal-Pro-Pro-2-(benzyloxy)ethyl ester FAB-MS: 686 (M+H$^+$)

I-75 $Me_2$Val-Val-MeVal-Pro-Pro-2-methoxyethyl ester FAB-MS: 610 (M+H$^+$)

I-174 $Me_2$Val-Val-MeVal-Pro-Pro-2-(4-methyl-5-thiazolyl) ethyl ester FAB-MS: 677.3 (M+H$^+$)

I-175 $Me_2$Val-Val-MeVal-Pro-Pro(2-methoxycarbonyl-2-methyl)-propyl ester FAB-MS: 666 (M+H$^+$)

I-172 $Me_2$Val-Val-MeVal-Pro-Pro-(1-methoxycarbonyl-2-methyl)-propyl ester FAB-MS: 666 (M+H$^+$)

III-4 $M_2$Val-Val-MeVal-Pro-Pro-2-propanone oxime ester FAB-MS: 607 (M+H$^+$)

III-34 $Me_2$Val-Val-MeVal-Pro-Pro-4-methylbenzaldehyde oxime ester FAB-MS: 669 (M+H$^+$)

III-35 $M_2$Val-Val-MeVal-Pro-Pro-benzophenone oxime ester FAB-MS: 731.5 (M+H$^+$)

The following compounds were prepared or can be prepared according to the example I-1

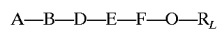  (Type I)

| No. | A | B | D | E | F | $R_L$ |
|---|---|---|---|---|---|---|
| I-1 | $Me_2$Val | Val | Val | Pro | Pro | Cyclohexyl |
| I-2 | $Me_2$Val | Val | Val | Pro | Pro | Cyclopentyl |
| I-3 | $Me_2$Val | Val | Val | Pro | Pro | Cyclopropyl |
| I-4 | $Me_2$Val | Val | Val | Pro | Pro | Cyclobutyl |
| I-5 | $Me_2$Val | Val | Val | Pro | Pro | Cycloheptyl |
| I-6 | $Me_2$Val | Val | Val | Pro | Pro | Cyclooctyl |
| I-7 | $Me_2$Val | Val | Val | Pro | Pro | Cyclononyl |
| I-8 | $Me_2$Val | Val | Val | Pro | Pro | 1-Methylpropyl |

-continued

| No. | A | B | D | E | F | R_L |
|---|---|---|---|---|---|---|
| I-9 | Me₂Val | Val | Val | Pro | Pro | 1-Methylbutyl |
| I-10 | Me₂Val | Val | Val | Pro | Pro | Cyclodecyl |
| I-13 | Me₂Val | Val | Val | Pro | Pro | Pentyl |
| I-14 | Me₂Val | Val | Val | Pro | Pro | Hexyl |
| I-15 | Me₂Val | Val | Val | Pro | Pro | Heptyl |
| I-16 | Me₂Val | Val | Val | Pro | Pro | Octyl |
| I-17 | Me₂Val | Val | Val | Pro | Pro | Nonyl |
| I-18 | Me₂Val | Val | Val | Pro | Pro | Decyl |
| I-19 | Me₂Val | Val | Val | Pro | Pro | Undecyl |
| I-20 | Me₂Val | Val | Val | Pro | Pro | Dodecyl |
| I-21 | Me₂Val | Val | Val | Pro | Pro | Tridecyl |
| I-22 | Me₂Val | Val | Val | Pro | Pro | Tetradecyl |
| I-23 | Me₂Val | Val | Val | Pro | Pro | Pentadecyl |
| I-24 | Me₂Val | Val | Val | Pro | Pro | Hexadecyl |
| I-25 | Me₂Val | Val | Val | Pro | Pro | Heptadecyl |
| I-26 | Me₂Val | Val | Val | Pro | Pro | Octadecyl |
| I-27 | Me₂Val | Val | Val | Pro | Pro | 1-Methylethyl |
| I-28 | Me₂Val | Val | Val | Pro | Pro | 2-Methylbutyl |
| I-29 | Me₂Val | Val | Val | Pro | Pro | 3-Methylbutyl |
| I-30 | Me₂Val | Val | Val | Pro | Pro | 2-Methylpropyl |
| I-31 | Me₂Val | Val | Val | Pro | Pro | 3,3-Dimethylbutyl |
| I-32 | Me₂Val | Val | Val | Pro | Pro | 2,3-Dimethylbutyl |
| I-33 | Me₂Val | Val | Val | Pro | Pro | 4-Methylpentyl |
| I-34 | Me₂Val | Val | Val | Pro | Pro | 4,4-Dimethylpentyl |
| I-35 | Me₂Val | Val | Val | Pro | Pro | Pent-3-yl |
| I-36 | Me₂Val | Val | Val | Pro | Pro | Hept-4-yl |
| I-37 | Me₂Val | Val | Val | Pro | Pro | 2,2-Dimethylbutyl |
| I-38 | Me₂Val | Val | Val | Pro | Pro | 2,2,2-Trifluoroethyl |
| I-39 | Me₂Val | Val | Val | Pro | Pro | 1-Fluoroethyl |
| I-40 | Me₂Val | Val | Val | Pro | Pro | 2,2-Difluoroethyl |
| I-41 | Me₂Val | Val | Val | Pro | Pro | Methylcyclopropyl |
| I-42 | Me₂Val | Val | Val | Pro | Pro | Methylcyclobutyl |
| I-43 | Me₂Val | Val | Val | Pro | Pro | Methylcyclopentyl |
| I-44 | Me₂Val | Val | Val | Pro | Pro | Methylcyclohexyl |
| I-45 | Me₂Val | Val | Val | Pro | Pro | Methylcycloheptyl |
| I-46 | Me₂Val | Val | Val | Pro | Pro | Methylcyclooctyl |
| I-47 | Me₂Val | Val | Val | Pro | Pro | Methylcyclononyl |
| I-48 | Me₂Val | Val | Val | Pro | Pro | Methylcyclodecyl |
| I-49 | Me₂Val | Val | Val | Pro | Pro | Methyladamantyl |
| I-50 | Me₂Val | Val | Val | Pro | Pro | 2-Propenyl |
| I-51 | Me₂Val | Val | Val | Pro | Pro | 3-Butenyl |
| I-52 | Me₂Val | Val | Val | Pro | Pro | 2-Butenyl |
| I-53 | Me₂Val | Val | Val | Pro | Pro | 2-Methyl-2-propenyl |
| I-54 | Me₂Val | Val | Val | Pro | Pro | 2-Pentenyl |
| I-55 | Me₂Val | Val | Val | Pro | Pro | 3-Methyl-2-propenyl |
| 1-56 | Me₂Val | Val | Val | Pro | Pro | 3-Pentenyl |
| I-57 | Me₂Val | Val | Val | Pro | Pro | 4-Pentenyl |
| I-58 | Me₂Val | Val | Val | Pro | Pro | 3-Methyl-2-butenyl |
| I-59 | Me₂Val | Val | Val | Pro | Pro | 3,7-Dimethyl-2,6-octadienyl |
| I-60 | Me₂Val | Val | Val | Pro | Pro | 3,7,11-Trimethyldodeca-2,6,10-trienyl |
| I-61 | Me₂Val | Val | Val | Pro | Pro | 3,7,11,15-Tetramethylhexadeca-2,6,10,14-tetraenyl |
| I-62 | Me₂Val | Val | Val | Pro | Pro | 1,3-Difluoro-prop-2-yl |
| I-63 | Me₂Val | Val | Val | Pro | Pro | 4-Piperidyl |
| I-64 | Me₂Val | Val | Val | Pro | Pro | N-Methyl-4-piperidyl |
| I-65 | Me₂Val | Val | Val | Pro | Pro | N-Acetyl-4-piperidyl |
| I-66 | Me₂Val | Val | Val | Pro | Pro | N-Formyl-4-piperidyl |
| I-67 | Me₂Val | Val | Val | Pro | Pro | N-tert-Butyl-4-piperidyl |
| I-68 | Me₂Val | Val | Val | Pro | Pro | N-tert-Butyloxy-carbonyl-4-piperidyl |
| I-69 | Me₂Val | Val | Val | Pro | Pro | N-Benzyl-4-piperidyl |
| I-70 | Me₂Val | Val | Val | Pro | Pro | N-Benzyloxycarbonyl-4-piperidyl |
| I-71 | Me₂Val | Val | Val | Pro | Pro | N-Benzoyl-4-piperidyl |
| I-72 | Me₂Val | Val | Val | Pro | Pro | 4-Tetrahydropyranyl |
| I-73 | Me₂Val | Val | Val | Pro | Pro | 4-Tetrahydrothienyl |
| I-74 | Me₂Val | Val | Val | Pro | Pro | 2-Hydroxyethyl |
| I-75 | Me₂Val | Val | Val | Pro | Pro | 2-Methoxyethyl |
| I-76 | Me₂Val | Val | Val | Pro | Pro | 2(2-Methoxy-ethoxy)-ethyl |
| I-77 | Me₂Val | Val | Val | Pro | Pro | 2-[2-(2-Methoxy-ethoxy)-ethoxy]ethyl |
| I-78 | Me₂Val | Val | Val | Pro | Pro | 2-(2-Butoxy-ethoxy)-ethyl |
| I-79 | Me₂Val | Val | Val | Pro | Pro | 2-Benzyloxy-ethyl |
| I-80 | Me₂Val | Val | Val | Pro | Pro | 2-Phenyloxy-ethyl |
| I-81 | Me₂Val | Val | Val | Pro | Pro | 2-Methylthioethyl |
| I-82 | Me₂Val | Val | Val | Pro | Pro | 2-Benzylthioethyl |
| I-83 | Me₂Val | Val | Val | Pro | Pro | 2-Phenylthioethyl |
| I-84 | Me₂Val | Val | Val | Pro | Pro | 2-Mercaptoethyl |
| I-85 | Me₂Val | Val | Val | Pro | Pro | 2-N,N-Dimethyl-aminoethyl |
| I-86 | Me₂Val | Val | Val | Pro | Pro | 2-N,N-Diethylamino-ethyl |
| I-87 | Me₂Val | Val | Val | Pro | Pro | 2-N-Acetylaminoethyl |
| I-88 | Me₂Val | Val | Val | Pro | Pro | 2-N-Benzoylamino-ethyl |
| I-89 | Me₂Val | Val | Val | Pro | Pro | 2-N-tert-Butyloxy-carbonylamino-ethyl |
| I-90 | Me₂Val | Val | Val | Pro | Pro | 2-N-Benzyloxycarbonylamino-ethyl |
| I-91 | Me₂Val | Val | Val | Pro | Pro | 2-(N-Isopropyl)-aminoethyl |
| I-92 | Me₂Val | Val | Val | Pro | Pro | 3-Methoxypropyl |
| I-93 | Me₂Val | Val | Val | Pro | Pro | 3-Benzyloxypropyl |
| I-94 | Me₂Val | Val | Val | Pro | Pro | 2,N,N-Diphenylamino-ethyl |
| I-95 | Me₂Val | Val | Val | Pro | Pro | 3-N,N-Dibenzylamino-propyl |
| I-96 | Me₂Val | Val | Val | Pro | Pro | 3-Phenyloxypropyl |
| I-97 | Me₂Val | Val | Val | Pro | Pro | 3-N,N-Dimethyl-aminopropyl |
| I-98 | Me₂Val | Val | Val | Pro | Pro | 3-N-Acetylaminopropyl |
| I-99 | Me₂Val | Val | Val | Pro | Pro | 3-N,N-Diethylamino-propyl |
| I-100 | Me₂Val | Val | Val | Pro | Pro | 3-Methylthiopropyl |
| I-101 | Me₂Val | Val | Val | Pro | Pro | 2-Phenylthiopropyl |
| I-102 | Me₂Val | Val | Val | Pro | Pro | 3-Benzylthiopropyl |
| I-111 | Me₂Val | Val | Val | Pro | Pro | (Indol-3-yl)methyl |
| I-112 | Me₂Val | Val | Val | Pro | Pro | (N-Methylindol-3-yl)methyl |
| I-113 | Me₂Val | Val | Val | Pro | Pro | (N-Acetylindol-3-yl)methyl |
| I-114 | Me₂Val | Val | Val | Pro | Pro | (3-N-Formylindolyl)-methyl |
| I-115 | Me₂Val | Val | Val | Pro | Pro | (1-Methylimidazolyl)methyl |
| I-116 | Me₂Val | Val | Val | Pro | Pro | (Thienyl-2-yl)methyl |
| I-117 | Me₂Val | Val | Val | Pro | Pro | (Benzimidazolyl)-methyl |
| I-118 | Me₂Val | Val | Val | Pro | Pro | (Isoxazol-5-yl)-methyl |
| I-119 | Me₂Val | Val | Val | Pro | Pro | (3-Methyl-isoxazol-5-yl)methyl |
| I-120 | Me₂Val | Val | Val | Pro | Pro | (3-Methoxymethyl-isoxazol-5-yl)methyl |
| I-121 | Me₂Val | Val | Val | Pro | Pro | (4-Methyl-imidazol-5-yl)methyl |
| I-123 | Me₂Val | Val | Val | Pro | Pro | (Furan-2-yl)methyl |
| I-124 | Me₂Val | Val | Val | Pro | Pro | (Furan-3-yl)methyl |
| I-125 | Me₂Val | Val | Val | Pro | Pro | (Benzofuran-2-yl)-methyl |
| I-126 | Me₂Val | Val | Val | Pro | Pro | (Thien-3-yl)methyl |
| I-127 | Me₂Val | Val | Val | Pro | Pro | (1-Benzylimidazol-3-yl)methyl |
| I-128 | Me₂Val | Val | Val | Pro | Pro | (Thiazol-2-yl)methyl |
| I-129 | Me₂Val | Val | Val | Pro | Pro | (Benzothiazol-2-yl)-methyl |
| I-130 | Me₂Val | Val | Val | Pro | Pro | Oxazol-2-yl)methyl |
| I-131 | Me₂Val | Val | Val | Pro | Pro | (Benzoxazol-2-yl)-methyl |
| I-132 | Me₂Val | Val | Val | Pro | Pro | (Thiazol-4-yl)methyl |
| I-133 | Me₂Val | Val | Val | Pro | Pro | (Thiazol-5-yl)methyl |
| I-134 | Me₂Val | Val | Val | Pro | Pro | (4-Methyl-thiazol-5-yl)methyl |
| I-135 | Me₂Val | Val | Val | Pro | Pro | (Oxazol-4-yl)methyl |
| I-136 | Me₂Val | Val | Val | Pro | Pro | (Oxazol-5-yl)methyl |
| I-137 | Me₂Val | Val | Val | Pro | Pro | (2-Phenyloxazol-4-yl)methyl |

-continued

| No. | A | B | D | E | F | R_L |
|---|---|---|---|---|---|---|
| I-138 | Me₂Val | Val | Val | Pro | Pro | (2-Phenylthiazol-4-yl)methyl |
| I-139 | Me₂Val | Val | Val | Pro | Pro | (2-Methyl-1,3,4-thiazol-5-yl)methyl |
| I-140 | Me₂Val | Val | Val | Pro | Pro | (2-Phenyl-1,3,4-thiazol-5-yl)methyl |
| I-141 | Me₂Val | Val | Val | Pro | Pro | Naphthylmethyl |
| I-142 | Me₂Val | Val | Val | Pro | Pro | Naphthyl-2-methyl |
| I-143 | Me₂Val | Val | Val | Pro | Pro | (4-Fluoro-phenyl)-methyl |
| I-144 | Me₂Val | Val | Val | Pro | Pro | (4-Methoxy-phenyl)-methyl |
| I-145 | Me₂Val | Val | Val | Pro | Pro | (4-Trifluoromethyl-phenyl)methyl |
| I-146 | Me₂Val | Val | Val | Pro | Pro | (4-Chlorophenyl)-methyl |
| I-147 | Me₂Val | Val | Val | Pro | Pro | (3,4-Dimethoxy-phenyl)methyl |
| I-148 | Me₂Val | Val | Val | Pro | Pro | (3,4-Dioxymethylene-phenyl)methyl |
| I-149 | Me₂Val | Val | Val | Pro | Pro | (3,4-Dioxyethylene-phenyl)methyl |
| I-150 | Me₂Val | Val | Val | Pro | Pro | (3-Fluoro-phenyl)methyl |
| I-151 | Me₂Val | Val | Val | Pro | Pro | (3-Methoxy-phenyl)methyl |
| I-152 | Me₂Val | Val | Val | Pro | Pro | (3-Trifluoromethyl-phenyl)methyl |
| I-153 | Me₂Val | Val | Val | Pro | Pro | (2-Fluoro-phenyl)methyl |
| I-154 | Me₂Val | Val | Val | Pro | Pro | (2,6-Difluoro-phenyl)methyl |
| I-155 | Me₂Val | Val | Val | Pro | Pro | (2-Trifluoromethyl-phenyl)methyl |
| I-156 | Me₂Val | Val | Val | Pro | Pro | (4-tert-Butylphenyl)-methyl |
| I-157 | Me₂Val | Val | Val | Pro | Pro | (4-Methyl-phenyl)methyl |
| I-158 | Me₂Val | Val | Val | Pro | Pro | (3-Pyridyl)methyl |
| I-159 | Me₂Val | Val | Val | Pro | Pro | (4-Pyridyl)methyl |
| I-160 | Me₂Val | Val | Val | Pro | Pro | (2-Pyridyl)methyl |
| I-161 | Me₂Val | Val | Val | Pro | Pro | (1-Naphthyl)methyl |
| I-162 | Me₂Val | Val | Val | Pro | Pro | (2-Naphthyl)methyl |
| I-163 | Me₂Val | Val | Val | Pro | Pro | (4-Quinolinyl)methyl |
| I-164 | Me₂Val | Val | Val | Pro | Pro | (5-Quinolinyl)methyl |
| I-165 | Me₂Val | Val | Val | Pro | Pro | (3-Methyl-phenyl)methyl |
| I-166 | Me₂Val | Val | Val | Pro | Pro | (Methoxycarbonyl)-methyl |
| I-167 | Me₂Val | Val | Val | Pro | Pro | (Methoxycarbonyl)-2-ethyl |
| I-168 | Me₂Val | Val | Val | Pro | Pro | (Methoxycarbonyl)-3-propyl |
| I-169 | Me₂Val | Val | Val | Pro | Pro | (Methoxycarbonyl)-4-butyl |
| I-170 | Me₂Val | Val | Val | Pro | Pro | (Methoxycarbonyl)-1-ethyl |
| I-171 | Me₂Val | yai | Val | Pro | Pro | (Methoxycarbonyl)-1,1-dimethyl-2-ethyl |
| I-172 | Me₂Val | Val | Val | Pro | Pro | (Methoxycarbonyl)-2-methyl-1-propyl |
| I-173 | Me₂Val | Val | Val | Pro | Pro | (Methoxycarbonyl)-1-propyl |
| I-174 | Me₂Val | Val | Val | Pro | Pro | 2-(4-Methyl-5-thiazolyl)ethyl |
| I-175 | Me₂Val | Val | Val | Pro | Pro | 2-Methoxycarbonyl-2-methylpropyl |
| I-401 | Me₂Val | Val | tert.Leu | Pro | Pro | Cyclohexyl |
| I-402 | Me₂Val | Val | tert.Leu | Pro | Pro | Cyclopentyl |
| I-403 | Me₂Val | Val | tert.Leu | Pro | Pro | Cyclopropyl |
| I-404 | Me₂Val | Val | tert.Leu | Pro | Pro | Cyclobutyl |
| I-405 | Me₂Val | Val | tert.Leu | Pro | Pro | Cycloheptyl |
| I-406 | Me₂Val | Val | tert.Leu | Pro | Pro | Cyclooctyl |
| I-407 | Me₂Val | Val | tert.Leu | Pro | Pro | Cyclononyl |
| I-408 | Me₂Val | Val | tert.Leu | Pro | Pro | 1-Methylpropyl |
| I-409 | Me₂Val | Val | tert.Leu | Pro | Pro | 1-Methylbutyl |
| I-410 | Me₂Val | Val | tert.Leu | Pro | Pro | Cyclodecyl |
| I-413 | Me₂Val | Val | tert.Leu | Pro | Pro | Pentyl |
| I-414 | Me₂Val | Val | tert.Leu | Pro | Pro | Hexyl |
| I-415 | Me₂Val | Val | tert.Leu | Pro | Pro | Heptyl |
| I-416 | Me₂Val | Val | tert.Leu | Pro | Pro | Octyl |
| I-417 | Me₂Val | Val | tert.Leu | Pro | Pro | Nonyl |
| I-418 | Me₂Val | Val | tert.Leu | Pro | Pro | Decyl |
| I-419 | Me₂Val | Val | tert.Leu | pro | Pro | Undecyl |
| I-420 | Me₂Val | Val | tert.Leu | Pro | Pro | Dodecyl |
| I-421 | Me₂Val | Val | tert.Leu | Pro | Pro | Tridecyl |
| I-422 | Me₂Val | Val | tert.Leu | Pro | Pro | Tetradecyl |
| I-423 | Me₂Val | Val | tert.Leu | Pro | Pro | Pentadecyl |
| I-424 | Me₂Val | Val | tert.Leu | Pro | Pro | Hexadecyl |
| I-425 | Me₂Val | Val | tert.Leu | Pro | Pro | Heptadecyl |
| I-426 | Me₂Val | Val | tert.Leu | Pro | Pro | Octadecyl |
| I-427 | Me₂Val | Val | tert.Leu | Pro | Pro | 1-Methylethyl |
| I-428 | Me₂Val | Val | tert.Leu | Pro | Pro | 2-Methylbutyl |
| I-429 | Me₂Val | Val | tert.Leu | Pro | Pro | 3-Methylbutyl |
| I-430 | Me₂Val | Val | tert.Leu | Pro | Pro | 2-Methylpropyl |
| I-431 | Me₂Val | Val | tert.Leu | Pro | Pro | 3,3-Dimethylbutyl |
| I-432 | Me₂Val | Val | tert.Leu | Pro | Pro | 2,3-Dimethylbutyl |
| I-433 | Me₂Val | Val | tert.Leu | Pro | Pro | 4-Methylpentyl |
| I-434 | Me₂Val | Val | tert.Leu | Pro | Pro | 4,4-Dimethylpentyl |
| I-435 | Me₂Val | Val | tert.Leu | Pro | Pro | Pent-3-yl |
| I-436 | Me₂Val | Val | tert.Leu | Pro | Pro | Hept-4-yl |
| I-437 | Me₂Val | Val | tert.Leu | Pro | Pro | 2,2-Dimethylbutyl |
| I-438 | Me₂Val | Val | tert.Leu | Pro | Pro | 2,2,2-Trifluoroethyl |
| I-439 | Me₂Val | Val | tert.Leu | Pro | Pro | 1-Fluoroethyl |
| I-440 | Me₂Val | Val | tert.Leu | Pro | Pro | 2,2-Difluoroethyl |
| I-441 | Me₂Val | Val | tert.Leu | Pro | Pro | Methylcyclopropyl |
| I-442 | Me₂Val | Val | tert.Leu | Pro | Pro | Methylcyclobutyl |
| I-443 | Me₂Val | Val | tert.Leu | Pro | Pro | Methylcyclopentyl |
| I-444 | Me₂Val | Val | tert.Leu | Pro | Pro | Methylcyclohexyl |
| I-445 | Me₂Val | Val | tert.Leu | Pro | Pro | Methylcycloheptyl |
| I-446 | Me₂Val | Val | tert.Leu | Pro | Pro | Methylcyclooctyl |
| I-447 | Me₂Val | Val | tert.Leu | Pro | Pro | Methylcyclononyl |
| I-448 | Me₂Val | Val | tert.Leu | Pro | Pro | Methylcyclodecyl |
| I-449 | Me₂Val | Val | tert.Leu | Pro | Pro | Methyladamantyl |
| I-450 | Me₂Val | Val | tert.Leu | Pro | Pro | 2-Propenyl |
| I-451 | Me₂Val | Val | tert.Leu | Pro | Pro | 3-Butenyl |
| I-452 | Me₂Val | Val | tert.Leu | Pro | Pro | 2-Butenyl |
| I-453 | Me₂Val | Val | tert.Leu | Pro | Pro | 2-Methyl-2-propenyl |
| I-454 | Me₂Val | Val | tert.Leu | Pro | Pro | 2-Pentenyl |
| I-455 | Me₂Val | Val | tert.Leu | Pro | Pro | 3-Methyl-2-propenyl |
| I-456 | Me₂Val | Val | tert.Leu | Pro | Pro | 3-Pentenyl |
| I-457 | Me₂Val | Val | tert.Leu | Pro | Pro | 4-Pentenyl |
| I-458 | Me₂Val | Val | tert.Leu | Pro | Pro | 3-Methyl-2-butenyl |
| I-459 | Me₂Val | Val | tert.Leu | Pro | Pro | 3,7-Dimethyl-2,6-octadienyl |
| I-460 | Me₂Val | Val | tert.Leu | Pro | Pro | 3,7,11-Trimethyl-dodeca-2,6,10-trienyl |
| I-461 | Me₂Val | Val | tert.Leu | Pro | Pro | 3,7,11,15-Tetra-methylhexadeca-2,6,10,14-tetraenyl |
| I-462 | Me₂Val | Val | tert.Leu | Pro | Pro | 1,3-Difluoro-prop-2-yl |
| I-463 | Me₂Val | Val | tert.Leu | Pro | Pro | 4-Piperidyl |
| I-464 | Me₂Val | Val | tert.Leu | Pro | Pro | N-Methyl-4-piperidyl |
| I-465 | Me₂Val | Val | tert.Leu | Pro | Pro | N-Acetyl-4-piperidyl |
| I-466 | Me₂Val | Val | tert.Leu | Pro | Pro | N-Formyl-4-piperidyl |
| I-467 | Me₂Val | Val | tert.Leu | Pro | Pro | N-tert-Butyl-4-piperidyl |
| I-468 | Me₂Val | Val | tert.Leu | Pro | Pro | N-tert-Butyloxycarbonyl-4-piperidyl |
| I-469 | Me₂Val | Val | tert.Leu | Pro | Pro | N-Benzyl-4-piperidyl |
| I-470 | Me₂Val | Val | tert.Leu | Pro | Pro | N-Benzyloxycarbonyl-4-piperidyl |
| I-471 | Me₂Val | Val | tert.Leu | Pro | Pro | N-Benzoyl-4-piperidyl |
| I-472 | Me₂Val | Val | tert.Leu | Pro | Pro | 4-Tetrahydropyranyl |
| I-473 | Me₂Val | Val | tert.Leu | Pro | Pro | 4-Tetrahydrothienyl |
| I-474 | Me₂Val | Val | tert.Leu | Pro | Pro | 2-Hydroxyethyl |
| I-475 | Me₂Val | Val | tert.Leu | Pro | Pro | 2-Methoxyethyl |
| I-476 | Me₂Val | Val | tert.Leu | Pro | Pro | 2(2-Methoxyethoxy)-ethyl |
| I-477 | Me₂Val | Val | tert.Leu | Pro | Pro | 2-[2-(2-Methoxy-ethoxy)ethoxy]ethyl |
| I-478 | Me₂Val | Val | tert.Leu | Pro | Pro | 2-(2-Butoxyethoxy)-ethyl |
| I-479 | Me₂Val | Val | tert.Leu | Pro | Pro | 2-Benzyloxyethyl |

| No. | A | B | D | E | F | $R_L$ |
|---|---|---|---|---|---|---|
| I-480 | Me$_2$Val | Val | tert.Leu | Pro | Pro | 2-Phenyloxyethyl |
| I-481 | Me$_2$Val | Val | tert.Leu | Pro | Pro | 2-Methylthioethyl |
| I-482 | Me$_2$Val | Val | tert.Leu | Pro | Pro | 2-Benzylthioethyl |
| I-483 | Me$_2$Val | Val | tert.Leu | Pro | Pro | 2-Phenylthioethyl |
| I-484 | Me$_2$Val | Val | tert.Leu | Pro | Pro | 2-Mercaptoethyl |
| I-485 | Me$_2$Val | Val | tert.Leu | Pro | Pro | 2-N,N-Dimethylaminoethyl |
| I-486 | Me$_2$Val | Val | tert.Leu | Pro | Pro | 2-N,N-Diethylaminoethyl |
| I-487 | Me$_2$Val | Val | tert.Leu | Pro | Pro | 2-N-Acetylaminoethyl |
| I-488 | Me$_2$Val | Val | tert.Leu | Pro | Pro | 2-N-Benzoylaminoethyl |
| I-489 | Me$_2$Val | Val | tert.Leu | Pro | Pro | 2-N-tert-Butyloxycarbonylaminoethyl |
| I-490 | Me$_2$Val | Val | tert.Leu | Pro | Pro | 2-N-Benzyloxycarbonylaminoethyl |
| I-491 | Me$_2$Val | Val | tert.Leu | Pro | Pro | 2-(N-Isopropyl)-aminoethyl |
| I-492 | Me$_2$Val | Val | tert.Leu | Pro | Pro | 3-Methoxypropyl |
| I-493 | Me$_2$Val | Val | tert.Leu | Pro | Pro | 3-Benzyloxypropyl |
| I-494 | Me$_2$Val | Val | tert.Leu | Pro | Pro | 2,N,N-Diphenylaminoethyl |
| I-495 | Me$_2$Val | Val | tert.Leu | Pro | Pro | 3-N,N-Dibenzylaminopropyl |
| I-496 | Me$_2$Val | Val | tert.Leu | Pro | Pro | 3-Phenyloxypropyl |
| I-497 | Me$_2$Val | Val | tert.Leu | Pro | Pro | 3-N,N-Dimethylaminopropyl |
| I-498 | Me$_2$Val | Val | tert.Leu | Pro | Pro | 3-N-Acetylaminopropyl |
| I-499 | Me$_2$Val | Val | tert.Leu | Pro | Pro | 3-N,N-Diethylaminopropyl |
| I-500 | Me$_2$Val | Val | tert.Leu | Pro | Pro | 3-Methylthiopropyl |
| I-501 | Me$_2$Val | Val | tert.Leu | Pro | Pro | 2-Phenylthiopropyl |
| I-502 | Me$_2$Val | Val | tert.Leu | Pro | Pro | 3-Benzylthiopropyl |
| I-511 | Me$_2$Val | Val | tert.Leu | Pro | Pro | (Indol-3-yl)methyl |
| I-512 | Me$_2$Val | Val | tert.Leu | Pro | Pro | (N-Methylindol-3-yl)methyl |
| I-513 | Me$_2$Val | Val | tert.Leu | Pro | Pro | (N-Acetylindol-3-yl)methyl |
| I-514 | Me$_2$Val | Val | tert.Leu | Pro | Pro | (3-N-Formylindolyl)methyl |
| I-515 | Me$_2$Val | Val | tert.Leu | Pro | Pro | (1-Methylimidazolyl)methyl |
| I-516 | Me$_2$Val | Val | tert.Leu | Pro | Pro | (Thienyl-2-yl)methyl |
| I-517 | Me$_2$Val | Val | tert.Leu | Pro | Pro | (Benzimidazolyl)methyl |
| I-518 | Me$_2$Val | Val | tert.Leu | Pro | Pro | (Isoxazol-5-yl)methyl |
| I-519 | Me$_2$Val | Val | tert.Leu | Pro | Pro | (3-Methylisoxazol-5-yl)methyl |
| I-520 | Me$_2$Val | Val | tert.Leu | Pro | Pro | (3-Methoxymethyl-isoxazol-5-yl)methyl |
| I-521 | Me$_2$Val | Val | tert.Leu | Pro | Pro | (4-Methyl-imidazol-5-yl)methyl |
| I-523 | Me$_2$Val | Val | tert.Leu | Pro | Pro | (Furan-2-yl)methyl |
| I-524 | Me$_2$Val | Val | tert.Leu | Pro | Pro | (Furan-3-yl)methyl |
| I-525 | Me$_2$Val | Val | tert.Leu | Pro | Pro | (Benzofuran-2-yl)methyl |
| I-526 | Me$_2$Val | Val | tert.Leu | Pro | Pro | (Thienyl-3-yl)methyl |
| I-527 | Me$_2$Val | Val | tert.Leu | Pro | Pro | (1-Benzylimidazol-3-yl)methyl |
| I-528 | Me$_2$Val | Val | tert.Leu | Pro | Pro | (Thiazol-2-yl)methyl |
| I-529 | Me$_2$Val | Val | tert.Leu | Pro | Pro | (Benzothiazol-2-yl)methyl |
| I-530 | Me$_2$Val | Val | tert.Leu | Pro | Pro | Oxazol-2-yl)methyl |
| I-531 | Me$_2$Val | Val | tert.Leu | Pro | Pro | (Benzoxazol-2-yl)methyl |
| I-532 | Me$_2$Val | Val | tert.Leu | Pro | Pro | (Thiazol-4-yl)methyl |
| I-533 | Me$_2$Val | Val | tert.Leu | Pro | Pro | (Thiazol-5-yl)methyl |
| I-534 | Me$_2$Val | Val | tert.Leu | Pro | Pro | (4-Methyl-thiazol-5-yl)methyl |
| I-535 | Me$_2$Val | Val | tert.Leu | Pro | Pro | (Oxazol-4-yl)methyl |
| I-536 | Me$_2$Val | Val | tert.Leu | Pro | Pro | (Oxazol-5-yl)methyl |
| I-537 | Me$_2$Val | Val | tert.Leu | Pro | Pro | (2-Phenyloxazol-4-yl)methyl |
| I-538 | Me$_2$Val | Val | tert.Leu | Pro | Pro | (2-Phenylthiazol-4-yl)methyl |
| I-539 | Me$_2$Val | Val | tert.Leu | Pro | Pro | (2-Methyl-1,3,4-thiazol-5-yl)methyl |
| I-540 | Me$_2$Val | Val | tert.Leu | Pro | Pro | (2-Phenyl-1,3,4-thiazol-5-yl)methyl |
| I-541 | Me$_2$Val | Val | tert.Leu | Pro | Pro | Naphthylmethyl |
| I-542 | Me$_2$Val | Val | tert.Leu | Pro | Pro | Naphthyl-2-methyl |
| I-543 | Me$_2$Val | Val | tert.Leu | Pro | Pro | (4-Fluoro-phenyl)-methyl |
| I-544 | Me$_2$Val | Val | tert.Leu | Pro | Pro | (4-Methoxyphenyl)-methyl |
| I-545 | Me$_2$Val | Val | tert.Leu | Pro | Pro | (4-Trifluoromethyl-phenyl)methyl |
| I-546 | Me$_2$Val | Val | tert.Leu | Pro | Pro | (4-Chlorophenyl)-methyl |
| I-547 | Me$_2$Val | Val | tert.Leu | Pro | Pro | (3,4-Dimethoxy-phenyl)methyl |
| I-548 | Me$_2$Val | Val | tert.Leu | Pro | Pro | (3,4-Dioxymethylene-phenyl)methyl |
| I-549 | Me$_2$Val | Val | tert.Leu | Pro | Pro | (3,4-Dioxyethylene-phenyl)methyl |
| I-550 | Me$_2$Val | Val | tert.Leu | Pro | Pro | (3-Fluorophenyl)-methyl |
| I-551 | Me$_2$Val | Val | tert.Leu | Pro | Pro | (3-Methoxy-phenyl)methyl |
| I-552 | Me$_2$Val | Val | tert.Leu | Pro | Pro | (3-Trifluoromethyl-phenyl)methyl |
| I-553 | Me$_2$Val | Val | tert.Leu | Pro | Pro | (2-Fluorophenyl)-methyl |
| I-554 | Me$_2$Val | Val | tert.Leu | Pro | Pro | (2,6-Difluorophenyl)-methyl |
| I-555 | Me$_2$Val | Val | tert.Leu | Pro | Pro | (2-Trifluoromethyl-phenyl)methyl |
| I-556 | Me$_2$Val | Val | tert.Leu | Pro | Pro | (4-tert-Butylphenyl)-methyl |
| I-557 | Me$_2$Val | Val | tert.Leu | Pro | Pro | (4-Methyl-phenyl)methyl |
| I-558 | Me$_2$Val | Val | tert.Leu | Pro | Pro | (3-Pyridyl)methyl |
| I-559 | Me$_2$Val | Val | tert.Leu | Pro | Pro | (4-Pyridyl)methyl |
| I-560 | Me$_2$Val | Val | tert.Leu | Pro | Pro | (2-Pyridyl)methyl |
| I-561 | Me$_2$Val | Val | tert.Leu | Pro | Pro | (1-Naphthyl)methyl |
| I-562 | Me$_2$Val | Val | tert.Leu | Pro | Pro | (2-Naphthyl)methyl |
| I-563 | Me$_2$Val | Val | tert.Leu | Pro | Pro | (4-Quinolinyl)methyl |
| I-564 | Me$_2$Val | Val | tert.Leu | Pro | Pro | (5-Quinolinyl)methyl |
| I-565 | Me$_2$Val | Val | tert.Leu | Pro | Pro | (3-Methyl-phenyl)methyl |
| I-566 | Me$_2$Val | Val | tert.Leu | Pro | Pro | (Methoxycarbonyl)-methyl |
| I-567 | Me$_2$Val | Val | tert.Leu | Pro | Pro | (Methoxycarbonyl)-2-ethyl |
| I-568 | Me2yal | Val | tert.Leu | Pro | Pro | (Methoxycarbonyl)-3-propyl |
| I-569 | Me$_2$Val | Val | tert.Leu | Pro | Pro | (Methoxycarbonyl)-4-butyl |
| I-570 | Me$_2$Val | Val | tert.Leu | Pro | Pro | (Methoxycarbonyl)-1-ethyl |
| I-571 | Me$_2$Val | Val | tert.Leu | Pro | Pro | (Methoxycarbonyl)-1,1-dimethyl-2-ethyl |
| I-572 | Me$_2$Val | Val | tert.Leu | Pro | Pro | (Methoxycarbonyl)-2-methyl-1-propyl |
| I-573 | Me$_2$Val | Val | tert.Leu | Pro | Pro | (Methoxycarbonyl)-1-propyl |
| I-201 | Me$_2$Val | tert.Leu | Val | Pro | Pro | Cyclohexyl |
| I-202 | Me$_2$Val | tert.Leu | Val | Pro | Pro | Cyclopentyl |
| I-203 | Me$_2$Val | tert.Leu | Val | Pro | Pro | Cyclopropyl |
| I-204 | Me$_2$Val | tert.Leu | Val | Pro | Pro | Cyclobutyl |
| I-205 | Me$_2$Val | tert.Leu | Val | Pro | Pro | Cycloheptyl |
| I-206 | Me$_2$Val | tert.Leu | Val | Pro | Pro | Cyclooctyl |
| I-207 | Me$_2$Val | tert.Leu | Val | Pro | Pro | Cyclononyl |
| I-208 | Me$_2$Val | tert.Leu | Val | Pro | Pro | 1-Methylpropyl |
| I-209 | Me$_2$Val | tert.Leu | Val | Pro | Pro | 1-Methylbutyl |
| I-210 | Me$_2$Val | tert.Leu | Val | Pro | Pro | Cyclodecyl |
| I-213 | Me$_2$Val | tert.Leu | Val | Pro | Pro | Pentyl |
| I-214 | Me$_2$Val | tert.Leu | Val | Pro | Pro | Hexyl |
| I-215 | Me$_2$Val | tert.Leu | Val | Pro | Pro | Heptyl |
| I-216 | Me$_2$Val | tert.Leu | Val | Pro | Pro | Octyl |
| I-217 | Me$_2$Val | tert.Leu | Val | Pro | Pro | Nonyl |
| I-218 | Me$_2$Val | tert.Leu | Val | Pro | Pro | Decyl |
| I-219 | Me$_2$Val | tert.Leu | Val | Pro | Pro | Undecyl |
| I-220 | Me$_2$Val | tert.Leu | Val | Pro | Pro | Dodecyl |

-continued

| No. | A | B | D | E | F | R_L |
|---|---|---|---|---|---|---|
| I-221 | Me₂Val | tert.Leu | Val | Pro | Pro | Tridecyl |
| I-222 | Me₂Val | tert.Leu | Val | Pro | Pro | Tetradecyl |
| I-223 | Me₂Val | tert.Leu | Val | Pro | Pro | Pentadecyl |
| I-224 | Me₂Val | tert.Leu | Val | Pro | Pro | Hexadecyl |
| I-225 | Me₂Val | tert.Leu | Val | Pro | Pro | Heptadecyl |
| I-226 | Me₂Val | tert.Leu | Val | Pro | Pro | Octadecyl |
| I-227 | Me₂Val | tert.Leu | Val | Pro | Pro | 1-Methylethyl |
| I-228 | Me₂Val | tert.Leu | Val | Pro | Pro | 2-Methylbutyl |
| I-229 | Me₂Val | tert.Leu | Val | Pro | Pro | 3-Methylbutyl |
| I-230 | Me₂Val | tert.Leu | Val | Pro | Pro | 2-Methylpropyl |
| I-231 | Me₂Val | tert.Leu | Val | Pro | Pro | 3,3-Dimethylbutyl |
| I-232 | Me₂Val | tert.Leu | Val | Pro | Pro | 2,3-Dimethylbutyl |
| I-233 | Me₂Val | tert.Leu | Val | Pro | Pro | 4-Methylpentyl |
| I-234 | Me₂Val | tert.Leu | Val | Pro | Pro | 4,4-Dimethylpentyl |
| I-235 | Me₂Val | tert.Leu | Val | Pro | Pro | Pent-3-yl |
| I-236 | Me₂Val | tert.Leu | Val | Pro | Pro | Hept-4-yl |
| I-237 | Me₂Val | tert.Leu | Val | Pro | Pro | 2,2-Dimethylbutyl |
| I-238 | Me₂Val | tert.Leu | Val | Pro | Pro | 2,2,2-Trifluoroethyl |
| I-239 | Me₂Val | tert.Leu | Val | Pro | Pro | 1-Fluoroethyl |
| I-240 | Me₂Val | tert.Leu | Val | Pro | Pro | 2,2-Difluoroethyl |
| I-241 | Me₂Val | tert.Leu | Val | Pro | Pro | Methylcyclopropyl |
| I-242 | Me₂Val | tert.Leu | Val | Pro | Pro | Methylcyclobutyl |
| I-243 | Me₂Val | tert.Leu | Val | Pro | Pro | Methylcyclopentyl |
| I-244 | Me₂Val | tert.Leu | Val | Pro | Pro | Methylcyclohexyl |
| I-245 | Me₂Val | tert.Leu | Val | Pro | Pro | Methylcycloheptyl |
| I-246 | Me₂Val | tert.Leu | Val | Pro | Pro | Methylcyclooctyl |
| I-247 | Me₂Val | tert.Leu | Val | Pro | Pro | Methylcyclononyl |
| I-248 | Me₂Val | tert.Leu | Val | Pro | Pro | Methylcyclodecyl |
| I-249 | Me₂Val | tert.Leu | Val | Pro | Pro | Methyladamentyl |
| I-250 | Me₂Val | tert.Leu | Val | Pro | Pro | 2-Propenyl |
| I-251 | Me₂Val | tert.Leu | Val | Pro | Pro | 3-Butenyl |
| I-252 | Me₂Val | tert.Leu | Val | Pro | Pro | 2-Butenyl |
| I-253 | Me₂Val | tert.Leu | Val | Pro | Pro | 2-Methyl-2-propenyl |
| I-254 | Me₂Val | tert.Leu | Val | Pro | Pro | 2-Pentenyl |
| I-255 | Me₂Val | tert.Leu | Val | Pro | Pro | 3-Methyl-2-propenyl |
| I-256 | Me₂Val | tert.Leu | Val | Pro | Pro | 3-Pentenyl |
| I-257 | Me₂Val | tert.Leu | Val | Pro | Pro | 4-Pentenyl |
| I-258 | Me₂Val | tert.Leu | Val | Pro | Pro | 3-Methyl-2-butenyl |
| I-259 | Me₂Val | tert.Leu | Val | Pro | Pro | 3,7-Dimethyl-2,6-octadienyl |
| I-260 | Me₂Val | tert.Leu | Val | Pro | Pro | 3,7,11-Trimethyl-dodeca-2,6,10-trienyl |
| I-261 | Me₂Val | tert.Leu | Val | Pro | Pro | 3,7,11,15-Tetramethyl-hexadeca-2,6,10,14-tetraenyl |
| I-262 | Me₂Val | tert.Leu | Val | Pro | Pro | 1,3-Difluoroprop-2-yl |
| I-263 | Me₂Val | tert.Leu | Val | Pro | Pro | 4-Piperidyl |
| I-264 | Me₂Val | tert.Leu | Val | Pro | Pro | N-Methyl-4-piperidyl |
| I-265 | Me₂Val | tert.Leu | Val | Pro | Pro | N-Acetyl-4-piperidyl |
| I-266 | Me₂Val | tert.Leu | Val | Pro | Pro | N-Formyl-4-piperidyl |
| I-267 | Me₂Val | tert.Leu | Val | Pro | Pro | N-tert-Butyl-4-piperidyl |
| I-268 | Me₂Val | tert.Leu | Val | Pro | Pro | N-tert-Butyloxy-carbonyl-4-piperidyl |
| I-269 | Me₂Val | tert.Leu | Val | Pro | Pro | N-Benzyl-4-piperidyl |
| I-270 | Me₂Val | tert.Leu | Val | Pro | Pro | N-Benzyloxycarbonyl-4-piperidyl |
| I-271 | Me₂Val | tert.Leu | Val | Pro | Pro | N-Benzoyl-4-piperidyl |
| I-272 | Me₂Val | tert.Leu | Val | Pro | Pro | 4-Tetrahydropyranyl |
| I-273 | Me₂Val | tert.Leu | Val | Pro | Pro | 4-Tetrahydrothienyl |
| I-274 | Me₂Val | tert.Leu | Val | Pro | Pro | 2-Hydroxyethyl |
| I-275 | Me₂Val | tert.Leu | Val | Pro | Pro | 2-Methoxyethyl |
| I-276 | Me₂Val | tert.Leu | Val | Pro | Pro | 2(2-Methoxyethoxy)-ethyl |
| I-277 | Me₂Val | tert.Leu | Val | Pro | Pro | 2-[2-(2-Methoxy-ethoxy)ethoxy]ethyl |
| I-278 | Me₂Val | tert.Leu | Val | Pro | Pro | 2-(2-Butoxyethoxy)-ethyl |
| I-279 | Me₂Val | tert.Leu | Val | Pro | Pro | 2-Benzyloxyethyl |
| I-280 | Me₂Val | tert.Leu | Val | Pro | Pro | 2-Phenoxyethyl |
| I-281 | Me₂Val | tert.Leu | Val | Pro | Pro | 2-Methylthioethyl |
| I-282 | Me₂Val | tert.Leu | Val | Pro | Pro | 2-Benzylthioethyl |
| I-283 | Me₂Val | tert.Leu | Val | Pro | Pro | 2-Phenylthioethyl |
| I-284 | Me₂Val | tert.Leu | Val | Pro | Pro | 2-Mercaptoethyl |
| I-285 | Me₂Val | tert.Leu | Val | Pro | Pro | 2-N,N-Dimethyl-aminoethyl |
| I-286 | Me₂Val | tert.Leu | Val | Pro | Pro | 2-N,N-Diethylamino-ethyl |
| I-287 | Me₂Val | tert.Leu | Val | Pro | Pro | 2-N-Acetylaminoethyl |
| I-288 | Me₂Val | tert.Leu | Val | Pro | Pro | 2-N-Benzoylamino-ethyl |
| I-289 | Me₂Val | tert.Leu | Val | Pro | Pro | 2-N-tert-Butyloxy-carbonylaminoethyl |
| I-290 | Me₂Val | tert.Leu | Val | Pro | Pro | 2-N-Benzyloxycarbon-ylamino-ethyl |
| I-291 | Me₂Val | tert.Leu | Val | Pro | Pro | 2-(N-Isopropyl)-aminoethyl |
| I-292 | Me₂Val | tert.Leu | Val | Pro | Pro | 3-Methoxypropyl |
| I-293 | Me₂Val | tert.Leu | Val | Pro | Pro | 3-Benzyloxypropyl |
| I-294 | Me₂Val | tert.Leu | Val | Pro | Pro | 2,N,N-Diphenylamino-ethyl |
| I-295 | Me₂Val | tert.Leu | Val | Pro | Pro | 3-N,N-Dibenzylamino-propyl |
| I-296 | Me₂Val | tert.Leu | Val | Pro | Pro | 3-Phenyloxypropyl |
| I-297 | Me₂Val | tert.Leu | Val | Pro | Pro | 3-N,N-Dimethyl-aminopropyl |
| I-298 | Me₂Val | tert.Leu | Val | Pro | Pro | 3-N-Acetylamino-propyl |
| I-299 | Me₂Val | tert.Leu | Val | Pro | Pro | 3-N,N-Diethylamino-propyl |
| I-300 | Me₂Val | tert.Leu | Val | Pro | Pro | 3-Methylthiopropyl |
| I-301 | Me₂Val | tert.Leu | Val | Pro | Pro | 2-Phenylthiopropyl |
| I-302 | Me₂Val | tert.Leu | Val | Pro | Pro | 3-Benzylthiopropyl |
| I-303 | Me₂Val | tert.Leu | Val | Pro | Pro | 2-Ethoxyethyl |
| I-304 | Me₂Val | tert.Leu | Val | Pro | Pro | 3-Ethoxypropyl |
| I-305 | Me₂Val | tert.Leu | Val | Pro | Pro | 4-Ethoxybutyl |
| I-311 | Me₂Val | tert.Leu | Val | Pro | Pro | (Indol-3-yl)methyl |
| I-312 | Me₂Val | tert.Leu | Val | Pro | Pro | (N-Methylindol-3-yl)methyl |
| I-313 | Me₂Val | tert.Leu | Val | Pro | Pro | (N-Acetylindol-3-yl)methyl |
| I-314 | Me₂Val | tert.Leu | Val | Pro | Pro | (3-N-Formylindolyl)-methyl |
| I-315 | Me₂Val | tert.Leu | Val | Pro | Pro | (1-Methylimidazo-lyl)methyl |
| I-316 | Me₂Val | tert.Leu | Val | Pro | Pro | (Thienyl-2-yl)methyl |
| I-317 | Me₂Val | tert.Leu | Val | Pro | Pro | (Benzimidazolyl)-methyl |
| I-318 | Me₂Val | tert.Leu | Val | Pro | Pro | (Isoxazol-5-yl)-methyl |
| I-319 | Me₂Val | tert.Leu | Val | Pro | Pro | (3-Methyl-isoxazol-5-yl)methyl |
| I-320 | Me₂Val | tert.Leu | Val | Pro | Pro | (3-Methoxymethyl-isoxazol-5-yl)methyl |
| I-321 | Me₂Val | tert.Leu | Val | Pro | Pro | (4-Methyl-imidazol-5-yl)methyl |
| I-323 | Me₂Val | tert.Leu | Val | Pro | Pro | (Furan-2-yl)methyl |
| I-324 | Me₂Val | tert.Leu | Val | Pro | Pro | (Furan-3-yl)methyl |
| I-325 | Me₂Val | tert.Leu | Val | Pro | Pro | (Benzofuran-2-yl)-methyl |
| I-326 | Me₂Val | tert.Leu | Val | Pro | Pro | (Thien-3-yl)methyl |
| I-327 | Me₂Val | tert.Leu | Val | Pro | Pro | (1-Benzylimidazol-3-yl)methyl |
| I-328 | Me₂Val | tert.Leu | Val | Pro | Pro | (Thiazol-2-yl)methyl |
| I-329 | Me₂Val | tert.Leu | Val | Pro | Pro | (Benzothiazol-2-yl)-methyl |
| I-330 | Me₂Val | tert.Leu | Val | Pro | Pro | Oxazol-2-yl)methyl |
| I-331 | Me₂Val | tert.Leu | Val | Pro | Pro | (Benzoxazol-2-yl)-methyl |
| I-332 | Me₂Val | tert.Leu | VaL | Pro | Pro | (Thiazol-4-yl)methyl |
| I-333 | Me₂Val | tert.Leu | Val | Pro | Pro | (Thiazol-5-yl)methyl |
| I-334 | Me₂Val | tert.Leu | Val | Pro | Pro | (4-Methyl-thiazol-5-yl)methyl |
| I-335 | Me₂Val | tert.Leu | Val | Pro | Pro | (Oxazol-4-yl)methyl |
| I-336 | Me₂Val | tert.Leu | Val | Pro | Pro | (Oxazol-5-yl)methyl |
| I-337 | Me₂Val | tert.Leu | Val | Pro | Pro | (2-Phenyloxazol-4-yl)methyl |
| I-338 | Me₂Val | tert.Leu | Val | Pro | Pro | (2-Phenylthiazol-4-yl)methyl |
| I-339 | Me₂Val | tert.Leu | Val | Pro | Pro | (2-Methyl-1,3,4-thiazol-5-yl)methyl |
| I-340 | Me₂Val | tert.Leu | Val | Pro | Pro | (2-Phenyl-1,3,4-thiazol-5-yl)methyl |
| I-341 | Me₂Val | tert.Leu | Val | Pro | Pro | Naphthylmethyl |

-continued

| No. | A | B | D | E | F | R_L |
|---|---|---|---|---|---|---|
| I-342 | Me₂Val | tert.Leu | Val | Pro | Pro | Naphthyl-2-methyl |
| I-343 | Me₂Val | tert.Leu | Val | Pro | Pro | (4-Fluoro-phenyl)methyl |
| I-344 | Me₂Val | tert.Leu | Val | Pro | Pro | (4-Methoxyphenyl)methyl |
| I-345 | Me₂Val | tert.Leu | Val | Pro | Pro | (4-Trifluoromethyl-phenyl)methyl |
| I-346 | Me₂Val | tert.Leu | Val | Pro | Pro | (4-Chlorophenyl)methyl |
| I-347 | Me₂Val | tert.Leu | Val | Pro | Pro | (3,4-Dimethoxy-phenyl)methyl |
| I-348 | Me₂Val | tert.Leu | Val | Pro | Pro | (3,4-Dioxymethylene-phenyl)methyl |
| I-349 | Me₂Val | tert.Leu | Val | Pro | Pro | (3,4-Dioxyethylene-phenyl)methyl |
| I-350 | Me₂Val | tert.Leu | Val | Pro | Pro | (3-Fluorophenyl)methyl |
| I-351 | Me₂Val | tert.Leu | Val | Pro | Pro | (3-Methoxyphenyl)methyl |
| I-352 | Me₂Val | tert.Leu | Val | Pro | Pro | (3-Trifluoromethyl-phenyl)methyl |
| I-353 | Me₂Val | tert.Leu | Val | Pro | Pro | (2-Fluorophenyl)methyl |
| I-354 | Me₂Val | tert.Leu | Val | Pro | Pro | (2,6-Difluorophenyl)methyl |
| I-355 | Me₂Val | tert.Leu | Val | Pro | Pro | (2-Trifluoromethyl-phenyl)methyl |
| I-356 | Me₂Val | tert.Leu | Val | Pro | Pro | (4-tert-Butylphenyl)methyl |
| I-357 | Me₂Val | tert.Leu | Val | Pro | Pro | (4-Methylphenyl)methyl |
| I-358 | Me₂Val | tert.Leu | Val | Pro | Pro | (3-Pyridyl)methyl |
| I-359 | Me₂Val | tert.Leu | Val | Pro | Pro | (4-Pyridyl)methyl |
| I-360 | Me₂Val | tert.Leu | Val | Pro | Pro | (2-Pyridyl)methyl |
| I-361 | Me₂Val | tert.Leu | Val | Pro | Pro | (1-Naphthyl)methyl |
| I-362 | Me₂Val | tert.Leu | Val | Pro | Pro | (2-Naphthyl)methyl |
| I-363 | Me₂Val | tert.Leu | Val | Pro | Pro | (4-Quinolinyl)methyl |
| I-364 | Me₂Val | tert.Leu | Val | Pro | Pro | (5-Quinolinyl)methyl |
| I-365 | Me₂Val | tert.Leu | Val | Pro | Pro | (3-Methylphenyl)methyl |
| I-366 | Me₂Val | tert.Leu | Val | Pro | Pro | (Methoxycarbonyl)methyl |
| I-367 | Me₂Val | tert.Leu | Val | Pro | Pro | (Methoxycarbonyl)-2-ethyl |
| I-368 | Me₂Val | tert.Leu | Val | Pro | Pro | (Methoxycarbonyl)-3-propyl |
| I-369 | Me₂Val | tert.Leu | Val | Pro | Pro | (Methoxycarbonyl)-4-butyl |
| I-370 | Me₂Val | tert.Leu | Val | Pro | Pro | (Methoxycarbonyl)-1-ethyl |
| I-371 | Me₂Val | tert.Leu | Val | Pro | Pro | (Methoxycarbonyl)-1,1-dimethyl-2-ethyl |
| I-372 | Me₂Val | tert.Leu | Val | Pro | Pro | (Methoxycarbonyl)-2-methyl-1-propyl |
| I-373 | Me₂Val | tert.Leu | Val | Pro | Pro | (Methoxycarbonyl)-1-propyl |

$$A-B-D-E-F-O-N\begin{subarray}{c}R_L^6\\R_L^5\end{subarray}$$ (Type (II))

| No. | A | B | D | E | F | $R_L^5$ | $R_L^6$ |
|---|---|---|---|---|---|---|---|
| II-1 | Me₂Val | Val | Val | Pro | Pro | H | Phenyl |
| II-2 | Me₂Val | Val | Val | Pro | Pro | H | Benzyl |
| II-3 | Me₂Val | Val | Val | Pro | Pro | H | 1-Methylethyl |
| II-4 | Me₂Val | Val | Val | Pro | Pro | H | 2-Methylpropyl |
| II-5 | Me₂Val | Val | Val | Pro | Pro | H | 1-Methylpropyl |
| II-6 | Me₂Val | Val | Val | Pro | Pro | H | 1,1-Dimethylethyl |
| II-7 | Me₂Val | Val | Val | Pro | Pro | H | Ethyl |
| II-8 | Me₂Val | Val | Val | Pro | Pro | H | Propyl |
| II-9 | Me₂Val | Val | Val | Pro | Pro | H | Butyl |
| II-10 | Me₂Val | Val | Val | Pro | Pro | H | Hexyl |
| II-11 | Me₂Val | Val | Val | Pro | Pro | H | Cyclopentyl |
| II-12 | Me₂Val | Val | Val | Pro | Pro | H | Cyclohexyl |
| II-13 | Me₂Val | Val | Val | Pro | Pro | H | Cycloheptyl |
| II-14 | Me₂Val | Val | Val | Pro | Pro | H | Pentyl |
| II-15 | Me₂Val | Val | Val | Pro | Pro | H | Trifluoromethyl |
| II-16 | Me₂Val | Val | Val | Pro | Pro | H | (4-Fluoro-phenyl)methyl |
| II-17 | Me₂Val | Val | Val | Pro | Pro | H | (4-Chloro-phenyl)methyl |
| II-18 | Me₂Val | Val | Val | Pro | Pro | H | (4-Methoxy-phenyl)methyl |
| II-19 | Me₂Val | Val | Val | Pro | Pro | H | (4-Trifluoro-methyl)phenyl-methyl |
| II-20 | Me₂Val | Val | Val | Pro | Pro | H | Cyclopropyl |
| II-21 | Me₂Val | Val | Val | Pro | Pro | H | 2-Propenyl |
| II-22 | Me₂Val | Val | Val | Pro | Pro | H | Cyclooctyl |
| II-23 | Me₂Val | Val | Val | Pro | Pro | H | Cyclononyl |
| II-24 | Me₂Val | Val | Val | Pro | Pro | H | Cyclodecyl |
| II-25 | Me₂Val | Val | Val | Pro | Pro | H | 2,2-Dimethylpropyl |
| II-26 | Me₂Val | Val | Val | Pro | Pro | H | tert-Butyl |
| II-27 | Me₂Val | Val | Val | Pro | Pro | Methyl | tert-Butyl |
| II-28 | Me₂Val | Val | Val | Pro | Pro | Methyl | Methyl |
| II-29 | Me₂Val | Val | Val | Pro | Pro | Ethyl | Ethyl |
| II-30 | Me₂Val | Val | Val | Pro | Pro | Methyl | Ethyl |
| II-31 | Me₂Val | Val | Val | Pro | Pro | Propyl | Propyl |
| II-32 | Me₂Val | Val | Val | Pro | Pro | Methyl | i-Methylethyl |
| II-33 | Me₂Val | Val | Val | Pro | Pro | Phenyl | Phenyl |
| II-34 | Me₂Val | Val | Val | Pro | Pro | Benzyl | Benzyl |
| II-35 | Me₂Val | Val | Val | Pro | Pro | Trifluoromethyl | Trifluoromethyl |
| II-36 | Me₂Val | Val | Val | Pro | Pro | (4-Chlorophenyl)methyl | (4-Chlorophenyl)methyl |
| II-37 | Me₂Val | Val | Val | Pro | Pro | (4-Trifluoromethylphenyl)methyl | (4-Trifluoromethylphenyl)methyl |
| II-38 | Me₂Val | Val | Val | Pro | Pro | H | (3-Fluorophenyl)methyl |
| II-39 | Me₂Val | Val | Val | Pro | Pro | H | (3-Chlorophenyl)methyl |
| II-40 | Me₂Val | Val | Val | Pro | Pro | H | (3-Methoxyphenyl)methyl |
| II-41 | Me₂Val | Val | Val | Pro | Pro | H | (4-tert-Butylphenyl)methyl |
| II-42 | Me₂Val | Val | Val | Pro | Pro | H | (4-Methylphenyl)methyl |
| II-43 | Me₂Val | Val | Val | Pro | Pro | H | (3-Methoxyphenyl)methyl |
| II-44 | Me₂Val | Val | Val | Pro | Pro | H | (2-Fluorophenyl)methyl |
| II-45 | Me₂Val | Val | Val | Pro | Pro | H | (2-Trifluoromethylphenyl)methyl |
| II-46 | Me₂Val | Val | Val | Pro | Pro | H | (3-Trifluoromethylphenyl)methyl |
| II-47 | Me₂Val | Val | Val | Pro | Pro | H | (2,6-Difluorophenyl)methyl |
| II-48 | Me₂Val | Val | Val | Pro | Pro | H | (3,4-Dimethoxyphenyl)methyl |
| II-49 | Me₂Val | Val | Val | Pro | Pro | H | (3,4-Dioxymethylene-phenyl)methyl |
| II-50 | Me₂Val | Val | Val | Pro | Pro | Methyl | Phenyl |
| II-51 | Me₂Val | Val | Val | Pro | Pro | Ethyl | Phenyl |

-continued

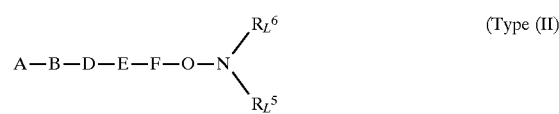 (Type (II))

| No. | A | B | D | E | F | $R^5_L$ and $R^6_L$ together |
|---|---|---|---|---|---|---|
| II-53 | Me$_2$Val | Val | Val | Pro | Pro |  |
| II-54 | Me$_2$Val | Val | Val | Pro | Pro |  |

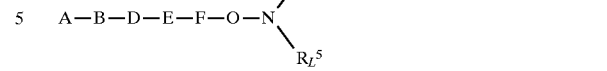 (Type (II))

| No. | A | B | D | E | F | $R^5_L$ and $R^6_L$ together |
|---|---|---|---|---|---|---|
| II-55 | Me$_2$Val | Val | Val | Pro | Pro | 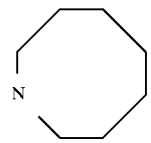 |

$$A-B-D-E-F-O-N=C\begin{matrix}R_L^6\\ \\R_L^5\end{matrix}$$ (Type (III))

| No. | A | B | D | E | F | $R^5_L$ | $R^6_L$ |
|---|---|---|---|---|---|---|---|
| III-1 | Me$_2$Val | Val | Val | Pro | Pro | H | Methyl |
| III-2 | Me$_2$Val | Val | Val | Pro | Pro | H | Ethyl |
| III-3 | Me$_2$Val | Val | Val | Pro | Pro | H | Propyl |
| III-4 | Me$_2$Val | Val | Val | Pro | Pro | Methyl | Methyl |
| III-5 | Me$_2$Val | Val | Val | Pro | Pro | Methyl | Ethyl |
| III-6 | Me$_2$Val | Val | Val | Pro | Pro | Ethyl | Ethyl |
| III-7 | Me$_2$Val | Val | Val | Pro | Pro | H | Phenyl |
| III-8 | Me$_2$Val | Val | Val | Pro | Pro | H | 4-Fluorophenyl |
| III-9 | Me$_2$Val | Val | Val | Pro | Pro | H | 4-Chlorophenyl |
| III-10 | Me$_2$Val | Val | Val | Pro | Pro | H | 4-Methoxyphenol |
| III-11 | Me$_2$Val | Val | Val | Pro | Pro | H | 4-Trifluoromethylphenyl |
| III-12 | Me$_2$Val | Val | Val | Pro | Pro | H | 4-tert-Butylphenyl |
| III-13 | Me$_2$Val | Val | Val | Pro | Pro | H | 3-Fluorophenyl |
| III-14 | Me$_2$Val | Val | Val | Pro | Pro | H | 3-Chlorophenyl |
| III-15 | Me$_2$Val | Val | Val | Pro | Pro | H | 3-Methoxyphenyl |
| III-16 | Me$_2$Val | Val | Val | Pro | Pro | H | 3-Trifluoromethylphenyl |
| III-17 | Me$_2$Val | Val | Val | Pro | Pro | H | 2-Fluorophenyl |
| III-18 | Me$_2$Val | Val | Val | Pro | Pro | H | 2-Trifluoromethylphenyl |
| III-19 | Me$_2$Val | Val | Val | Pro | Pro | H | tert-Butyl |
| III-20 | Me$_2$Val | Val | Val | Pro | Pro | Methyl | tert-Butyl |
| III-21 | Me$_2$Val | Val | Val | Pro | Pro | H | 2,6-Difluorophenyl |
| III-22 | Me$_2$Val | Val | Val | Pro | Pro | H | 2-Methylpropyl |
| III-23 | Me$_2$Val | Val | Val | Pro | Pro | H | 2,2-Dimethylpropyl |
| III-24 | Me$_2$Val | Val | Val | Pro | Pro | H | Butyl |
| III-25 | Me$_2$Val | Val | Val | Pro | Pro | H | Pentyl |
| III-26 | Me$_2$Val | Val | Val | Pro | Pro | H | Hexyl |
| III-27 | Me$_2$Val | Val | Val | Pro | Pro | H | Heptyl |
| III-28 | Me$_2$Val | Val | Val | Pro | Pro | H | Octyl |
| III-29 | Me$_2$Val | Val | Val | Pro | Pro | H | Nonyl |
| III-30 | Me$_2$Val | Val | Val | Pro | Pro | H | Cyclopropyl |
| III-31 | Me$_2$Val | Val | Val | Pro | Pro | H | Cyclobutyl |
| III-32 | Me$_2$Val | Val | Val | Pro | Pro | H | Cyclopentyl |
| III-33 | Me$_2$Val | Val | Val | Pro | Pro | H | Cyclohexyl |
| III-34 | Me$_2$Val | Val | Val | Pro | Pro | H | 4-Methylphenyl |
| III-35 | Me$_2$Val | Val | Val | Pro | Pro | Phenyl | Phenyl |
| III-36 | Me$_2$Val | Val | Val | Pro | Pro | H | 1-Naphthyl |
| III-37 | Me$_2$Val | Val | Val | Pro | Pro | H | 2-Naphthyl |
| III-38 | Me$_2$Val | Val | Val | Pro | Pro | Methyl | 1-Naphthyl |
| III-39 | Me$_2$Val | Val | Val | Pro | Pro | Methyl | 2-Naphthyl |
| III-40 | Me$_2$Val | Val | Val | Pro | Pro | Methyl | Phenyl |
| III-41 | Me$_2$Val | Val | Val | Pro | Pro | Methyl | 4-Fluorophenyl |

$$A-B-D-E-F-O-N=C\diagup\begin{matrix}R_L^6\\R_L^5\end{matrix}\qquad\text{(Type (III))}$$

| No. | A | B | D | E | F | $R^5_L$ | $R^6_L$ |
|---|---|---|---|---|---|---|---|
| III-42 | Me₂Val | Val | Val | Pro | Pro | Methyl | 4-Chlorophenyl |
| III-43 | Me₂Val | Val | Val | Pro | Pro | Methyl | 4-Methoxyphenyl |
| III-44 | Me₂Val | Val | Val | Pro | Pro | Methyl | 4-Trifluoro-methylphenyl |
| III-45 | Me₂Val | Val | Val | Pro | Pro | Methyl | 4-Methylphenyl |
| III-46 | Me₂Val | Val | Val | Pro | Pro | Methyl | 4-tert-Butyl-phenyl |
| III-47 | Me₂Val | Val | Val | Pro | Pro | Methyl | 3,4-Dimethoxy-phenyl |
| III-48 | Me₂Val | Val | Val | Pro | Pro | H | 3,4-Dimethoxy-phenyl |
| III-49 | Me₂Val | Val | Val | Pro | Pro | Methyl | 3-Fluorophenyl |
| III-50 | Me₂Val | Val | Val | Pro | Pro | Methyl | 3-Chlorophenyl |
| III-51 | Me₂Val | Val | Val | Pro | Pro | Methyl | 3-Methoxyphenyl |
| III-52 | Me₂Val | Val | Val | Pro | Pro | Methyl | 3-Trifluoro-methylphenyl |
| III-53 | Me₂Val | Val | Val | Pro | Pro | Methyl | 2-Fluorophenyl |
| III-54 | Me₂Val | Val | Val | Pro | Pro | Methyl | 2-Chlorophenyl |
| III-55 | Me₂Val | Val | Val | Pro | Pro | Methyl | 2-Trifluoro-methylphenyl |
| III-56 | Me₂Val | Val | Val | Pro | Pro | Methyl | 2,6-Difluoro-phenyl |
| III-57 | Me₂Val | Val | Val | Pro | Pro | Tri-fluoro-methyl | Phenyl |
| III-58 | Me₂Val | Val | Val | Pro | Pro | Tri-fluoro-methyl | 2-Naphthyl |
| III-59 | Me₂Val | Val | Val | Pro | Pro | H | Tetrahydro-2-furanyl |
| III-60 | Me₂Val | Val | Val | Pro | Pro | H | Tetrahydro-3-furanyl |
| III-61 | Me₂Val | Val | Val | Pro | Pro | H | 2-Thienyl |
| III-62 | Me₂Val | Va1 | Val | Pro | Pro | H | Tetrahydro-2-furanyl |
| III-63 | Me₂Val | Val | Val | Pro | Pro | H | 3-Thienyl |
| III-64 | Me₂Val | Val | Val | Pro | Pro | H | 5-Methyl-imidazol-4-yl |
| III-65 | Me₂Val | Val | Val | Pro | Pro | H | 3-Indolyl |
| III-66 | Me₂Val | Val | Val | Pro | Pro | Methyl | 2-Thioenyl |
| III-67 | Me₂Val | Val | Val | Pro | Pro | Methyl | 2-Pyrrolyl |
| III-68 | Me₂Val | Val | Val | Pro | Pro | Methyl | Thiazol-4-yl |
| III-69 | Me₂Val | Val | Val | Pro | Pro | Methyl | Oxazol-4-yl |
| III-70 | Me₂Val | Val | Val | Pro | Pro | H | 2-Phenyl-thiazol-4-yl |
| III-71 | Me₂Val | Val | Val | Pro | Pro | Methyl | 2-Phenyl-thiazol-4-yl |
| III-72 | Me₂Val | Val | Val | Pro | Pro | H | 2-Phenyl-oxazol-4-yl |
| III-73 | Me₂Val | Val | Val | Pro | Pro | Methyl | 2-Phenyl-oxazol-4-yl |
| III-74 | Me₂Val | Val | Val | Pro | Pro | H | 2-Pyrrolyl |
| III-76 | Me₂Val | Val | Val | Pro | Pro | Methyl | 2-Pyrrolyl |
| III-77 | Me₂Val | Val | Val | Pro | Pro | H | N-Methyl-2-pyrrolyl |
| III-78 | Me₂Val | Val | Val | Pro | Pro | Methyl | Benzo-2-furyl |
| III-79 | Me₂Val | Val | Val | Pro | Pro | Methyl | 2-Thiophenyl |
| III-80 | Me₂Val | Val | Val | Pro | Pro | Methyl | 3-Thiophenyl |
| III-81 | Me₂Val | Val | Val | Pro | Pro | H | 3-Phenyl-isoxazol-5-yl |
| III-82 | Me₂Val | Val | Val | Pro | Pro | H | 3-Methyl-isoxazol-5-yl |
| III-83 | Me₂Val | Val | Val | Pro | Pro | H | 3-Isopropyl-5-isoxazolyl |
| III-84 | Me₂Val | Val | Val | Pro | Pro | Methyl | 3-Phenyl-isoxazol-5-yl |
| III-85 | Me₂Val | Val | Val | Pro | Pro | Methyl | 3-Methyl-isoxazol-5-yl |
| III-86 | Me₂Val | Val | Val | Pro | Pro | Cyclo-propyl | 2-Thienyl |
| III-87 | Me₂Val | Val | Val | Pro | Pro | Methyl | Imidazol-4-yl |
| III-88 | Me₂Val | Val | Val | Pro | Pro | H | 4-Pyridyl |

-continued $$A-B-D-E-F-O-N=C\begin{matrix}R_L^6\\R_L^5\end{matrix} \quad \text{(Type (III))}$$

| No. | A | B | D | E | F | $R^5_L$ | $R^6_L$ |
|---|---|---|---|---|---|---|---|
| III-89 | Me₂Val | Val | Val | Pro | Pro | H | 3-Pyridyl |
| III-90 | Me₂Val | Val | Val | Pro | Pro | H | 2-Pyridyl |
| III-91 | Me₂Val | Val | Val | Pro | Pro | Methyl | 4-Pyridyl |
| III-92 | Me₂Val | Val | Val | Pro | Pro | Methyl | 3-Pyridyl |
| III-93 | Me₂Val | Val | Val | Pro | Pro | Methyl | 2-Pyridyl |
| III-94 | Me₂Val | Val | Val | Pro | Pro | H | 4-Quinolinyl |
| III-95 | Me₂Val | Val | Val | Pro | Pro | Methyl | 4-Quinolinyl |
| III-96 | Me₂Val | Val | Val | Pro | Pro | H | 5-Quinolinyl |
| III-97 | Me₂Val | Val | Val | Pro | Pro | Methyl | 5-Quinolinyl |
| III-109 | Me₂Val | Val | Val | Pro | Pro | Cyclopropyl | |
| III-110 | Me₂Val | Val | Val | Pro | Pro | Cyclobutyl | |
| III-111 | Me₂Val | Val | Val | Pro | Pro | Cyclopentyl | |
| III-112 | Me₂Val | Val | Val | Pro | Pro | Cyclohexyl | |
| III-113 | Me₂Val | Val | Val | Pro | Pro | Cycloheptyl | |
| III-114 | Me₂Val | Val | Val | Pro | Pro | Cyclooctyl | |
| III-115 | Me₂Val | Val | Val | Pro | Pro | Cyclononyl | |
| III-116 | Me₂Val | Val | Val | Pro | Pro | Cyclodecyl | |
| III-117 | Me₂Val | Val | Val | Pro | Pro | 4-Piperidyl | |
| III-118 | Me₂Val | Val | Val | Pro | Pro | 4-Pyranyl | |
| III-119 | Me₂Val | Val | Val | Pro | Pro | 4-Thiophenyl | |
| III-120 | Me₂Val | Val | Val | Pro | Pro | 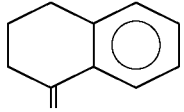 | |
| III-121 | Me₂Val | Val | Val | Pro | Pro | 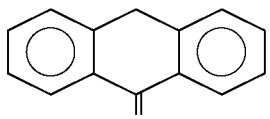 | |
| III-122 | Me₂Val | Val | Val | Pro | Pro | 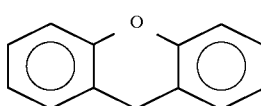 | |
| III-123 | Me₂Val | Val | Val | Pro | Pro | 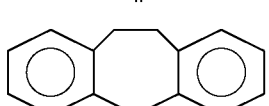 | |
| III-122 | Me₂Val | Val | Val | Pro | Pro | 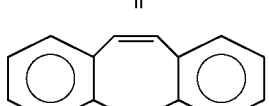 | |

D. Biological Evaluation

1. In vitro methodology

Cytotoxicity may be measured using a standard methodology for adherent cell lines such as the microculture tetrazolium assay (MTT). Details of this assay have been published (Alley, MC et al, Cancer Research 48:589–601, 1988). Exponentially growing cultures of tumor cells such as the HT-29 colon carcinoma or LX-1 lung tumor are used to make microtiter plate cultures. Cells are seeded at 5000–20,000 cells per well in 96-well plates (in 150 μl of media), and grown overnight at 37° C. Test compounds are added, in 10-fold dilutions varying from $10^{-4}$M to $10^{-10}$M. Cells are then incubated for 48 hours. To determine the number of viable cells in each well, the MTT dye is added (50 μl of 3 mg/ml solution of 3-(4,5-dimethylthiazol-2-yl)-2,5-diphenyltetrazolium bromide in saline). This mixture is incubated at 37° C. for 5 hours, and then 50 μl of 25% SDS, pH2 is added to each well. After an overnight incubation, the absorbance of each well at 550 nm is read using an ELISA reader. The values for the mean +/− SD of data from replicated wells are calculated, using the formula % T/C (% viable cells treated/control).

 $\times 100 = \% \ T/C$

The concentration of test compound which gives a T/C of 50% growth inhibition was designated as the $IC_{50}$ 2. In vivo methodology Compounds of this invention may be further tested in any of the various pre-clinical assays for in vivo activity which are indicative of clinical utility. Such assays are conducted with nude mice into which tumor tissue, preferably of human origin, has been transplanted ("xenografted"), as is well known in this field. Test compounds are evaluated for their anti-tumor efficacy following administration to the xenograft-bearing mice.

More specifically, human tumors which have been grown in athymic nude mice are transplanted into new recipient animals, using tumor fragments which are about 50 mg in size. The day of transplantation is designated as day 0. Six to ten days later, mice are treated with the test compounds given as an intravenous or intraperitoneal injection, in groups of 5–10 mice at each dose.

Compounds were given daily for 5 days, 10 days or 15 days, at doses from 10–100 mg/kg body weight. Tumor diameters and body weights were measured twice weekly. Tumor volumes are calculated using the diameters measured with Vernier calipers, and the formula:

(length×width$^2$)/2=mg of tumor weight

Mean tumor weights are calculated for each treatment group, and T/C values determined for each group relative to the untreated control tumors.

The novel compounds of the present invention show good in vitro activity in the above mentioned assay systems and antitumor activity in the above mentioned in vivo system.

We claim:

1. A peptide of the formula I

A—B—D—E—F—L  (I)

and the salts thereof with physiologically tolerated acids, wherein:

A is of Formula II$_A$,

  (II$_A$)

wherein
$R_A$ is hydrogen, $C_{1-3}$-alkyl, $C_{1-3}$-alkyl which is substituted by 1 to 3 fluorine atoms, cyclopropyl, or cyclopropyl which is substituted by 1 to 3 fluorine atoms;
$R^1_A$ is $C_{1-3}$-alkyl, $C_{1-3}$-alkyl which is substituted by 1 to 3 fluorine atoms, cyclopropyl, or cyclopropyl which is substituted by 1 to 3 fluorine atoms;
$R^2_A$ is $C_{1-5}$-alkyl, $C_{1-5}$-alkyl which is substituted by 1 to 3 fluorine atoms, $C_{3-5}$-cycloalkyl, or $C_{3-5}$-cycloalkyl which is substituted by 1 to 3 fluorine atoms;

B is of Formula II$_B$,

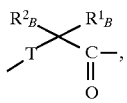  (II$_B$)

wherein
T is an NH group,
$R^1_B$ is a hydrogen;
$R^2_B$ is $C_{1-6}$-alkyl, $C_{3-6}$-cycloalkyl, methoxymethyl, 1-methoxyethyl or 1-methylvinyl; or
$R^1_B$ and $R^2_B$ together are an isopropylidene group; or
T is an oxygen atom,
$R^1_B$ is hydrogen and
$R^2_B$ is $C_{1-6}$-alkyl;

D is of Formula II$_D$,

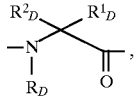  (II$_D$)

wherein
$R_D$ is hydrogen, $C_{1-3}$-alkyl, $C_{1-3}$-alkyl which is substituted by 1 to 3 fluorine atoms, cyclopropyl, or cyclopropyl which is substituted by 1 to 3 fluorine atoms;
$R^1_D$ is hydrogen; and
$R^2_D$ is $C_{1-5}$-alkyl, cyclopropyl, methoxymethyl, 1-methoxyethyl or 1-methylvinyl;

E is of Formula II$_E$

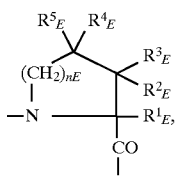  (II$_E$)

wherein
$n_E$ is 0, 1 or 2;
$R^1_E$ is hydrogen, $C_{1-3}$-alkyl, $C_{1-3}$-alkyl which is substituted by 1 to 3 fluorine atoms, cyclopropyl, or cyclopropyl which is substituted by 1 to 3 fluorine atoms;
$R^2_E$ and $R^3_E$ are, independently of one another, hydrogen or a methyl group;
$R^4_E$ is hydrogen, a hydroxy, methoxy or ethoxy group or a fluorine atom; and
$R^5_E$ is hydrogen or a fluorine atom; or
$n_E$ is 1 and
$R^3_E$ and $R^4_E$ together are a bond; or
$R^4_E$ and $R^5_E$ are a doubly bonded oxygen radical; or
$n_E$ is 2 and $R^1_E$ and $R^2_E$ together are a bond; or E is of Formula III$_E$,

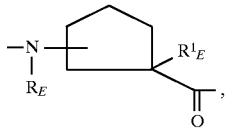  (III$_E$)

wherein
$R_E$ is hydrogen or a methyl or ethyl group; and
$R^1_E$ is hydrogen, $C_{1-3}$-alkyl, $C_{1-3}$-alkyl which is substituted by 1 to 3 fluorine atoms, cyclopropyl, or cyclopropyl which is substituted by 1 to 3 fluorine atoms; or E is of Formula $IV_E$

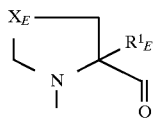  (IV$_E$)

wherein
$X_E$ is an oxygen or a sulfur atom; and
$R1_E$ is hydrogen, $C_{1-3}$-alkyl, $C_{1-3}$-alkyl which is substituted by 1 to 3 fluorine atoms, cyclopropyl, or cyclopropyl which is substituted by 1 to 3 fluorine atoms;

F is of Formula $II_F$,

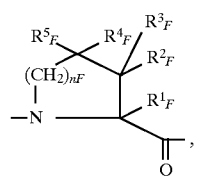  (II$_F$)

wherein
$n_F$ is 0, 1 or 2;
$R^1_F$ is hydrogen, $C_{1-3}$-alkyl, $C_{1-3}$-alkyl which is substituted by 1 to 3 fluorine atoms, cyclopropyl, or cyclopropyl which is substituted by 1 to 3 fluorine atoms;
$R^2_F$ and $R^3_F$ are, independently of one another, hydrogen or a methyl group;
$R^4_F$ is hydrogen, a hydroxy, methoxy or ethoxy group or a fluorine atom; and
$R^5_F$ is hydrogen or a fluorine atom; or
$n_F$ is 1 and $R^3_F$ and $R^4_E$ together are a bond; or F is of Formula $III_F$,

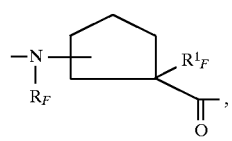  (III$_F$)

wherein
$R^1_F$ is hydrogen, $C_{1-3}$-alkyl, $C_{1-3}$-alkyl which is substituted by 1 to 3 fluorine atoms, cyclopropyl, or cyclopropyl which is substituted by 1 to 3 fluorine atoms;
$R^2_F$ and $R^3_F$ are, independently of one another, hydrogen or a methyl group;
$R^4_F$ is hydrogen, a hydroxy, methoxy or ethoxy group of a fluorine atom; and
$R^5_F$ is hydrogen or a fluorine atom or
$n_E$ is 1 and $R^3_F$ and $R^4_F$ together are a bond; or F is of Formula $IV_F$,

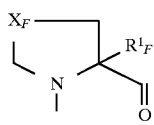

wherein
$X_F$ is oxygen or sulfur; and
$R^1_F$ is hydrogen, $C_{1-3}$-alkyl, $C_{1-3}$-alkyl which is substituted by 1 to 3 fluorine atoms, cyclopropyl, or cyclopropyl which is substituted by 1 to 3 fluorine atoms; or F is an N-methylglycyl, N-ethylglycyl, N-methylalanyl or N-ethylalanyl residue; and
L is a substituted or unsubstituted, $C^1$–$C_{18}$ alkoxy, aryloxy, hydroxylamino, or oxime group.

2. A peptide of the formula I as claimed in claim 1, where L is a radical of the formula $I_L$

  (I$_L$)

where
$R_L$ is $C_{3-10}$-cycloalkyl, a $C_{2-18}$-methylalkenyl or $C_{5-16}$-alkyl, $C_{1-5}$-alkylcarboxy-$C_{1-10}$-alkyl which may be substituted by 1 to 5 halogen atoms; or
$R_L$ is the radical —$(CH_2)_{aL}$—$R_L{}^1$, where
$a_L$ is 1, 2 or 3, and
$R_L{}^1$ is a saturated or partially unsaturated $C_{3-10}$-carbocycle, or
a saturated or partially unsaturated cyclic radical which, besides carbon atoms, contains as ring members hetero atoms from the group consisting of oxygen, sulfur or nitrogen, it being possible in saturated systems for the nitrogen additionally to be bonded to a $C_{1-4}$-alkyl, $C_{1-4}$-acyl, $C_{1-4}$-alkoxyacyl group, a benzyl or benzoyl group; or
$R_L$ is the radical —$[CH_2$—$CH$=$C(CH_3)$—$CH_2]_{bL}$—H where
$b_L$ is 1, 2, 3 or 4; or
$R_L$ is —$(CH_2$—$CH_2$—$O)_{dL}$—$CH_3$ where
dL is 1, 2, 3, 4 or 5; or
$R_L$ is —$(CH_2)_{eL}$-aryl or —$(CH_2)_{eL}$-hetaryl (with the restriction that $R_L$ is not benzyl), it being possible for the aryl or hetaryl radical to be substituted or unsubstituted, and
$_{eL}$ is 0, 1, 2 or 3; or
$R_L$ is a radical of the formula

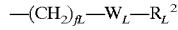  (II$_L$)

where
fL is 2, 3 or 4,
$W_L$ is a bridge formed from oxygen, sulfur or the

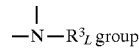

where
$R_L{}^2$ is hydrogen, $C_{1-4}$-alkyl-, $C_{3-7}$-cycloalkyl or substituted or unsubstituted aryl or methylaryl,
$R_L{}^3$ is hydrogen, $C_{1-4}$-alkyl, $C_{3-7}$-cycloalkyl, $C_{1-18}$-alkanoyl, benzoyl, carbonyloxy-$C_{1-4}$-alkyl, carbonyloxybenzyl or substituted or unsubstituted aryl or methylaryl; or
$R_L$ is a radical of the formula

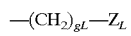  (III$_L$)

where
$g_L$ is 2, 3 or 4 and
$Z_L$ is formyl, aminocarbonyl, hydrazinocarbonyl or an acyclic or cyclic acetal or thioacetal radical; or
$R_L$ is a radical of the formula

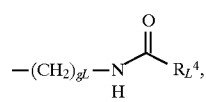  (IV$_L$)

where
$g_L$ has the abovementioned meaning, and $R_L^4$ has the meaning of glycol residues of the formula —O—(CH$_2$—CH$_2$)$_{h_L}$—CH$_3$, where $h_L$ is a number from 40 to 90, and the salts thereof with physiologically tolerated acids.

3. A peptide of the formula I as claimed in claim 1, where L is

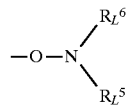 (V$_L$)

where $R_L^5$ is hydrogen, C$_1$–C$_8$-alkyl which can be substituted by up to 6 halogen atoms, preferably fluorine, C$_{3-10}$-cycloalkyl, C$_{1-4}$-alkyl-C$_{3-10}$- cycloalkyl, substituted or unsubstituted aryl or hetaryl or C$_{1-4}$-alkylaryl which can be substituted by 1 to 5 halogen atoms, and $R_L^6$ is C$_1$–C$_8$-alkyl which can be substituted by up to 6 halogen atoms, preferably fluorine, C$_{3-10}$-cycloalkyl, C$_{1-4}$-alkyl-C$_{3-10}$- cycloalkyl, substituted or unsubstituted aryl or hetaryl or C$_{1-4}$-alkylaryl which can be substituted by 1 to 5 halogen atoms, or 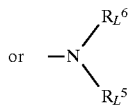

forms a 5-, 6- or 7-membered heterocycle, and the salts thereof with physiologically tolerated acids.

4. A peptide of the formula I as claimed in claim 1, where L is an oxime residue of the formula VI$_L$

 (VI$_L$)

where $R_L^5$ and $R_L^6$ each have the abovementioned meanings, or

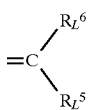

together form a 3- to 7-membered cyclic system which may be aromatic-fused, and the salts thereof with physiologically tolerated acids.

5. A peptide of the formula I

A—B—D—E—F—L  (I)

and the salts thereof with physiologically tolerated acids, wherein:

A is N,N-dimethylvalyl;

B is valyl or tert-leucyl;

D is valyl or tert-leucyl;

E and F are each prolyl; and

L is a substituted or unsubstituted C$_1$–C$_{18}$ alkoxy, aryloxy, hydroxylamino, or oxime group.

* * * * *